(12) United States Patent
Carter

(10) Patent No.: US 7,098,669 B2
(45) Date of Patent: Aug. 29, 2006

(54) DEPTH DETERMINING SYSTEM

(75) Inventor: Larry Carter, Fountain Valley, CA (US)

(73) Assignee: Flowline, Inc., Los Alamitos, CA (US)

( * ) Notice: Subject to any disclaimer, the term of this patent is extended or adjusted under 35 U.S.C. 154(b) by 38 days.

(21) Appl. No.: 10/945,419

(22) Filed: Sep. 20, 2004

(65) Prior Publication Data

US 2005/0072227 A1    Apr. 7, 2005

Related U.S. Application Data

(60) Provisional application No. 60/507,897, filed on Oct. 1, 2003.

(51) Int. Cl.
*G01R 27/02* (2006.01)

(52) U.S. Cl. .................. 324/605; 324/607; 324/644

(58) Field of Classification Search ............... 324/605, 324/607, 644
See application file for complete search history.

(56) References Cited

U.S. PATENT DOCUMENTS

| | | |
|---|---|---|
| 2,188,628 A | 1/1940 | Freystedt |
| 2,852,937 A | 9/1958 | Maze |
| 3,243,702 A | 3/1966 | Schuck |
| 3,535,637 A | 10/1970 | Goransson |
| 3,680,365 A | 8/1972 | Summers |
| 3,710,244 A | 1/1973 | Rauchwerger |
| 3,720,813 A | 3/1973 | Badessa |
| 3,740,533 A | 6/1973 | van Zeggelaar |
| 3,797,311 A | 3/1974 | Blanchard et al. |
| 3,864,974 A | 2/1975 | Rauchwerger |
| 3,890,836 A | 6/1975 | McKenzie et al. |
| 3,913,084 A | 10/1975 | Bollinger et al. |
| 3,958,159 A | 5/1976 | Rauchwerger |
| 4,000,650 A | 1/1977 | Snyder |
| 4,101,865 A | 7/1978 | Schurr |
| 4,130,018 A | 12/1978 | Adams et al. |
| 4,145,914 A | 3/1979 | Newman |
| 4,170,765 A | 10/1979 | Austin et al. |
| 4,176,396 A | 11/1979 | Howatt |
| 4,183,007 A | 1/1980 | Baird |
| 4,201,085 A | 5/1980 | Larson |
| 4,201,093 A | 5/1980 | Logan |
| 4,264,788 A | 4/1981 | Keidel et al. |
| 4,295,370 A | 10/1981 | Bristol |

(Continued)

FOREIGN PATENT DOCUMENTS

EP          1 164 385 A2     12/2001

(Continued)

*Primary Examiner*—Diane Lee
*Assistant Examiner*—Timothy J. Dole
(74) *Attorney, Agent, or Firm*—Sheppard, Mullin, Richter & Hampton LLP

(57) ABSTRACT

A system for determining the depth of a fluid in a storage tank. The depth of the fluid is determined after the detection of a pulsed wave that is reflected from the top surface of the fluid. The system includes a transducer, an analog-to-digital converter, and a filter. The transducer is configured to sense the reflected pulsed wave and to generate an analog input signal that corresponds to the reflected pulsed wave. The analog-to-digital converter is coupled to the transducer, and configured to convert the analog input signal into a digital input signal. The filter is coupled to the analog-to-digital converter. The filter includes a finite impulse response filter that is configured to receive the digital input signal and to generate a digital output signal.

29 Claims, 18 Drawing Sheets

U.S. PATENT DOCUMENTS

| | | |
|---|---|---|
| 4,404,841 A | 9/1983 | Franke et al. |
| 4,480,476 A | 11/1984 | Samodovitz |
| 4,530,372 A | 7/1985 | Overton et al. |
| 4,570,155 A | 2/1986 | Skarman et al. |
| 4,596,144 A | 6/1986 | Panton et al. |
| 4,603,581 A | 8/1986 | Yamanoue et al. |
| 4,619,002 A | 10/1986 | Thro |
| 4,671,124 A | 6/1987 | Seliga |
| 4,676,100 A | 6/1987 | Eichberger |
| 4,716,536 A | 12/1987 | Blanchard |
| 4,868,797 A | 9/1989 | Soltz |
| 4,984,449 A | 1/1991 | Caldwell et al. |
| 5,017,909 A | 5/1991 | Goekler |
| 5,031,068 A | 7/1991 | Hansen, III et al. |
| 5,099,454 A | 3/1992 | Dieulesaint et al. |
| 5,111,683 A | 5/1992 | Fond |
| 5,131,271 A | 7/1992 | Haynes et al. |
| 5,162,748 A | 11/1992 | Katz |
| 5,245,333 A | 9/1993 | Anderson et al. |
| 5,317,520 A | 5/1994 | Castle |
| D350,297 S | 9/1994 | Weisel |
| 5,345,426 A | 9/1994 | Lipschutz |
| D352,010 S | 11/1994 | Curbbun |
| 5,372,029 A | 12/1994 | Brandes |
| 5,483,501 A | 1/1996 | Park et al. |
| D367,915 S | 3/1996 | Daugherty |
| 5,513,531 A | 5/1996 | Sapia et al. |
| 5,546,005 A | 8/1996 | Rauchwerger |
| 5,550,790 A | 8/1996 | Velamoor et al. |
| 5,553,479 A | 9/1996 | Rauchwerger |
| 5,578,764 A | 11/1996 | Yokoi et al. |
| 5,737,963 A | 4/1998 | Eckert et al. |
| 5,822,274 A | 10/1998 | Haynie et al. |
| 5,895,848 A | 4/1999 | Wilson et al. |
| 5,930,200 A | 7/1999 | Kabel |
| 5,996,407 A | 12/1999 | Hewitt |
| 6,484,088 B1 | 11/2002 | Reimer |
| 6,545,946 B1 * | 4/2003 | Huss et al. .................... 367/99 |

FOREIGN PATENT DOCUMENTS

| | | |
|---|---|---|
| WO | WO 91/05226 | 4/1991 |
| WO | WO 91/08443 | 6/1991 |
| WO | WO 95/19559 | 7/1995 |

* cited by examiner

DEPTH DETERMINING SYSTEM

CROSS-REFERENCE TO RELATED APPLICATION

Priority is claimed under 35 U.S.C. § 119(e) to U.S. Provisional Patent Application No. 60/507,897, filed on Oct. 1, 2003, entitled: "DEPTH DETERMINING SYSTEM AND RELATED METHOD" by Larry Carter, which application is incorporated by reference herein.

BACKGROUND OF THE INVENTION

1. Field of the Invention

The invention relates generally to the field of determining the level of a fluid in a storage tank. More specifically, the invention relates to an apparatus for measuring the time of receipt for a reflected acoustic wave.

2. Description of the Related Art

The level of a fluid in a storage tank can be measured using various techniques. In one technique, a transducer is connected to the bottom surface of the storage tank. The transducer is excited by a pulse from a function generator. The vibration from the transducer excites a pulsed wave in the fluid within the storage tank, which propagates upward toward the fluid-gas interface, i.e., the interface between the top of the fluid and the gas above the fluid. At the fluid-gas interface, a portion of the wave is reflected back toward the transducer where it is received. Based on the reflected wave, the transducer generates an electrical signal, which is provided to a processing system. The processing system calculates the distance from the transducer to the top of the fluid, and thus, the depth of the fluid in the storage tank, based on the known value of the speed of sound through the fluid and the time measured for the wave to propagate from the transducer to the fluid/air interface and back to the transducer.

Accordingly, an accurate calculation of the depth of the fluid in the storage tank is dependent upon an accurate determination of the time at which the reflected wave is received at the transducer. It should, therefore, be appreciated that there is a need for an ultrasonic measurement system and method that accurately calculates the depth of a fluid in a storage tank by accurately determining the time of receipt of the reflected wave. The present invention satisfies this need.

SUMMARY OF THE INVENTION

Embodiments of the present invention include an ultrasonic measurement system that provides an accurate depth measurement of a fluid in a storage tank by accurately determining the time of receipt of a reflected wave induced in the storage tank by a transducer.

An exemplary embodiment of the present invention is a system for determining the depth of a fluid in a storage tank. The depth of the fluid is determined after the detection of a pulsed wave that is reflected from the top surface of the fluid. The system includes a transducer, an analog-to-digital converter, and a filter. The transducer is configured to sense the reflected pulsed wave and to generate an analog input signal that corresponds to the reflected pulsed wave. The analog-to-digital converter is coupled to the transducer, and configured to convert the analog input signal into a digital input signal. The filter is coupled to the analog-to-digital converter. The filter includes a finite impulse response filter that is configured to receive the digital input signal and to generate a digital output signal. The finite impulse response filter includes an n-stage shift register, where n is an even integer that is greater than or equal to four, n/2 subtractors coupled to the n-stage shift register, and n/2−1 adders coupled to the n-stage shift register.

In other, more detailed features of the invention, each subtractor of the n/2 subtractors has a first input terminal, a second input terminal that is coupled to a stage of the n-stage shift register, and an output terminal. Also, each adder of the n/2−1 adders has a first input terminal that is coupled to an output terminal of a subtractor, and a second input terminal that is coupled to a stage of the n-stage shift register. In addition, the first input terminal of one of the n/2 subtractors is coupled to that first stage of the n-stage shift register, and each of the first input terminals of the other subtractors is coupled to an output terminal of an adder.

In other, more detailed features of the invention, the finite impulse response filter is configured to calculate a digital output signal at time $t_1$, Output($t_1$), based on the digital input signal at time $t_1$, Input($t_1$), a digital output signal at time $t_0$, Output($t_0$), and a data value in an nth stage of the n-stage shift register at time $t_0$, $X_{n-1}(t_0)$. Where $t_1$ is the time at a next clock cycle after time $t_0$ and Output($t_1$) is calculated based on the following equation: Output($t_1$)=Input ($t_1$)−(Output($t_0$)+$X_{n-1}(t_0)$).

In other, more detailed features of the invention, the system further includes a threshold and peak detector, a control circuit, and a storage device. The threshold and peak detector is coupled to the filter. The threshold and peak detector is configured to compare an amplitude of the digital output signal from the finite impulse response filter to a threshold value and to create a list of peaks, including an amplitude value and a time of each peak that exceeds the threshold value, in real time. The control circuit is coupled to both the filter and the threshold and peak detector. The control circuit is configured to receive the list of peaks from the threshold and peak detector. The storage device is coupled to the control circuit, and is configured to store the list of peaks received by the control circuit.

In other, more detailed features of the invention, the system further includes a signal generator and a driver. The signal generator is coupled between the control circuit and the transducer, and is configured to generate a generator signal that is used to stimulate the transducer to induce the pulsed wave. The driver is coupled between the signal generator and the transducer, and is configured to amplify the generator signal before the generator signal is coupled into to the transducer. Also, the filter includes a matched filter that is configured to compare the analog input to the generator signal.

In other, more detailed features of the invention, the control circuit calculates a value of the depth of the fluid in the storage tank based on the list of peaks. Also, the control circuit generates a digital pulse-width-modulated signal that varies in modulation based on the depth of the fluid in the storage tank. The system further includes a digital-to-analog converter and a level-signaling circuit. The digital-to-analog converter is coupled to the control circuit and configured to convert the digital pulse-width-modulated signal into an analog pulse-width-modulated signal. The level-signaling circuit is coupled to the digital-to-analog converter, and is configured to convert the analog pulse-width-modulated signal into a level-signaling output signal that correlates to the depth of the fluid in the storage tank.

In other, more detailed features of the invention, the system further includes a temperature sensor that is coupled to the control circuit. The temperature sensor is configured to provide the control circuit with a temperature value for the fluid in the storage tank. The control circuit adjusts the calculated value of the depth of the fluid in the storage tank based on the temperature value for the fluid in the storage tank.

In other, more detailed features of the invention, the threshold and peak detector recalculates the threshold value based on the value of the amplitude values of the digital output signal. Also, the system further includes an amplifier that is coupled between the transducer and the analog-to-digital converter. The amplifier is configured to amplify the analog input signal.

In other, more detailed features of the invention, the filter includes a complex filter having a first finite impulse response filter and a second finite impulse response filter that sample the digital input signal at twice the frequency of the pulsed wave. The sampled digital input signal filtered by the first finite impulse response filter is 90° out of phase with respect to the sampled digital input signal filtered by the second finite impulse response filter. Also, the filter calculates a square root of a sum of squares value of a signal output from the first finite impulse response filter and a signal output from the second finite impulse response filter.

In other, more detailed features of the invention, the filter calculates an approximate value of a square root of a sum of squares value by adding the larger of an absolute value of a signal output from the first finite impulse response filter and an absolute value of a signal output from the second finite impulse response filter to $3/8$ times the smaller of the absolute value of the signal output from the first finite impulse response filter and the absolute value of the signal output from the second finite impulse response filter. The approximate value of the square root of the sum of squares value is calculated by shifting the n-stage shift register to the right twice for the first or second finite impulse response filter that has the smaller absolute value of output signal; adding an output of the twice right-shifted, n-stage shift register to the output of the first or second finite impulse response filter that has the larger absolute value, resulting in a first added value; shifting the n-stage shift register having the smaller absolute value of output signal once more to the right; and adding the output of the thrice right-shifted, n-stage shift register to the first added value.

In other, more detailed features of the invention, the filter is configured to determine the phase difference between the digital input signal and the coefficients that define the filter.

Another exemplary embodiment of the invention is a system for determining the depth of a fluid in a storage tank. The depth of the fluid is determined after the detection of a pulsed wave that is reflected from the top surface of the fluid. The system includes a transducer, an analog-to-digital converter, and a filter. The transducer is configured to sense the reflected pulsed wave and to generate an analog input signal that corresponds to the reflected pulsed wave. The analog-to-digital converter is coupled to the transducer, and configured to convert the analog input signal into a digital input signal. The filter is coupled to the analog-to-digital converter. The filter includes a finite impulse response filter that is configured to receive the digital input signal and to generate a digital output signal. The finite impulse response filter includes an n-stage shift register, where n is an integer that is greater than one, a subtractor that is coupled to the n-stage shift register, an adder that is coupled to both the n-stage shift register and the subtractor, and a storage register that is coupled to both the adder and the subtractor.

In other, more detailed features of the invention, the subtractor has a first input terminal that is coupled to one of the stages of the n-stage shift register, a second input terminal, and an output terminal. The adder has a first input terminal that is coupled to another of the stages of the n-stage shift register, a second input terminal, and an output terminal that is coupled to the subtractor's second input terminal. The storage register has an input terminal that is coupled to the subtractor's output terminal, and an output terminal that is coupled to the adder's second input terminal.

Another exemplary embodiment of the invention is a system for determining the depth of a fluid in a storage tank. The depth of the fluid is determined after the detection of a pulsed wave that is reflected from the top surface of the fluid. The system includes a transducer, an analog-to-digital converter, and a filter. The transducer is configured to measure the reflected pulsed wave, and to generate an analog input signal that corresponds to the reflected pulsed wave. The analog-to-digital converter is coupled to the transducer, and configured to convert the analog input signal into a digital input signal. The filter is coupled to the analog-to-digital converter. The filter includes a finite impulse response filter that is configured to receive the digital input signal and to generate a digital output signal. The finite impulse response filter includes a two-stage shift register, a first subtractor that is coupled to the two-stage shift register, an n/2-stage shift register that is coupled to the first subtractor, where n is an even integer greater than or equal to four, a second subtractor that is coupled to both the first subtractor and the n/2-stage shift register, an adder that is coupled to the second subtractor, and a storage register that is coupled to the adder.

In other, more detailed features of the invention, the first subtractor has two input terminals and an output terminal, and each of the first subtractor input terminals is coupled to one of the stages of the two-stage shift register. The n/2-stage shift register has an input terminal that is coupled to the output terminal of the first subtractor. The second subtractor has a first input terminal that is coupled to the output terminal of the first subtractor, a second input terminal that is coupled to the n/2th stage of the n/2-stage shift register, and an output terminal. The adder has a first input terminal that is coupled to the second subtractor's output terminal, a second input terminal, and an output terminal. The storage register has an input terminal that is coupled to the adder's output terminal, and an output terminal that is coupled to the adder's second input terminal.

Another exemplary embodiment of the invention is a finite impulse response filter that includes an n-stage shift register, where n is an even integer that is greater than or equal to four, n/2 subtractors that are coupled to the n-stage shift register, and n/2−1 adders that are coupled to the n-stage shift register. Each subtractor of the n/2 subtractors has a first input terminal, a second input terminal that is coupled to a stage of the n-stage shift register, and an output terminal. Each adder of the n/2−1 adders has a first input terminal that is coupled to an output terminal of a subtractor, and a second input terminal that is coupled to a stage of the n-stage shift register. The first input terminal of one of the n/2 subtractors is coupled to the first stage of the n-stage shift register, and the first input terminal of each of the other subtractors is coupled to an output terminal of an adder.

Another exemplary embodiment of the invention is a finite impulse response filter that includes an n-stage shift register, where n is an integer that is greater than one, a subtractor, an adder, and a storage register. The subtractor has a first input terminal that is coupled to one of the stages of the n-stage shift register, a second input terminal, and an output terminal. The adder has a first input terminal that is coupled to another of the stages of the n-stage shift register, a second input terminal, and an output terminal that is coupled to the subtractor's second input terminal. The storage register has an input terminal that is coupled to the subtractor's output terminal, and an output terminal that is coupled to the adder's second input terminal.

Another exemplary embodiment of the invention is a finite impulse response filter that includes a two-stage shift register, a first subtractor, an n/2-stage shift register, where n is an even integer greater than or equal to four, a second subtractor, an adder, and a storage register. The first subtractor has two input terminals and an output terminal. Each of the first subtractor input terminals is coupled to one of the stages of the two-stage shift register. The n/2-stage shift register has an input terminal that is coupled to the output terminal of the first subtractor. The second subtractor has a first input terminal that is coupled to the output terminal of the first subtractor, a second input terminal that is coupled to the n/2th stage of the n/2-stage shift register, and an output terminal. The adder has a first input terminal that is coupled to the second subtractor's output terminal, a second input terminal, and an output terminal. The storage register has an input terminal that is coupled to the adder's output terminal, and an output terminal that is coupled to the adder's second input terminal.

Other features of the invention should become apparent from the following description of the preferred embodiments taken in conjunction with the accompanying drawings, which illustrate, by way of example, the principles of the invention.

DETAILED DESCRIPTION OF THE PREFERRED EMBODIMENTS

Figure 1B:
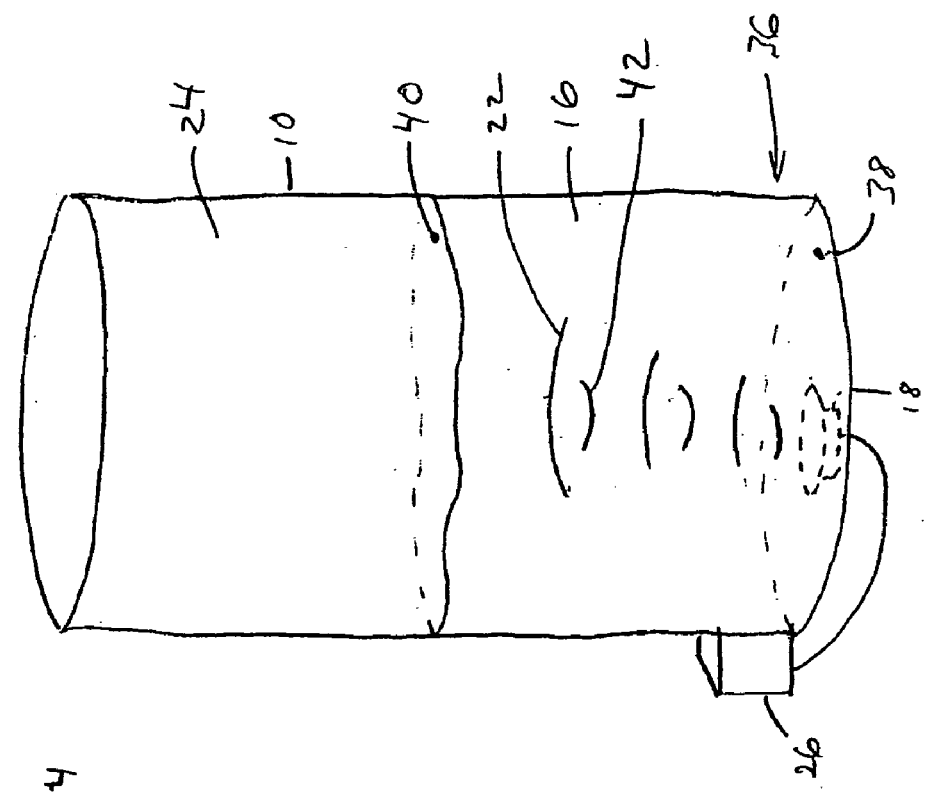
FIG. 1b is perspective drawing of an ultrasonic depth determining device having a transducer mounted to the bottom of a storage tank containing a fluid according to another preferred embodiment.
Figure 1A:
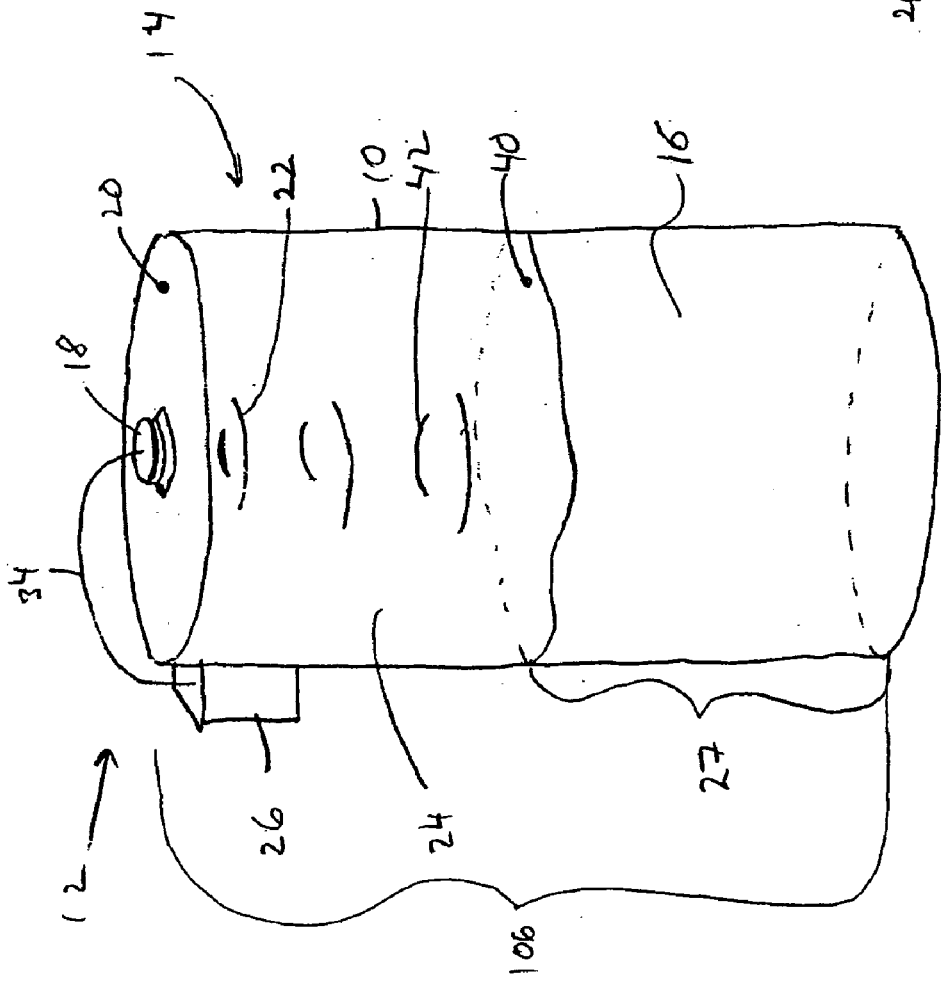
FIG. 1a is perspective drawing of an ultrasonic depth determining device having a transducer mounted to the top of a storage tank containing a fluid according to a preferred embodiment.
Figure 2:
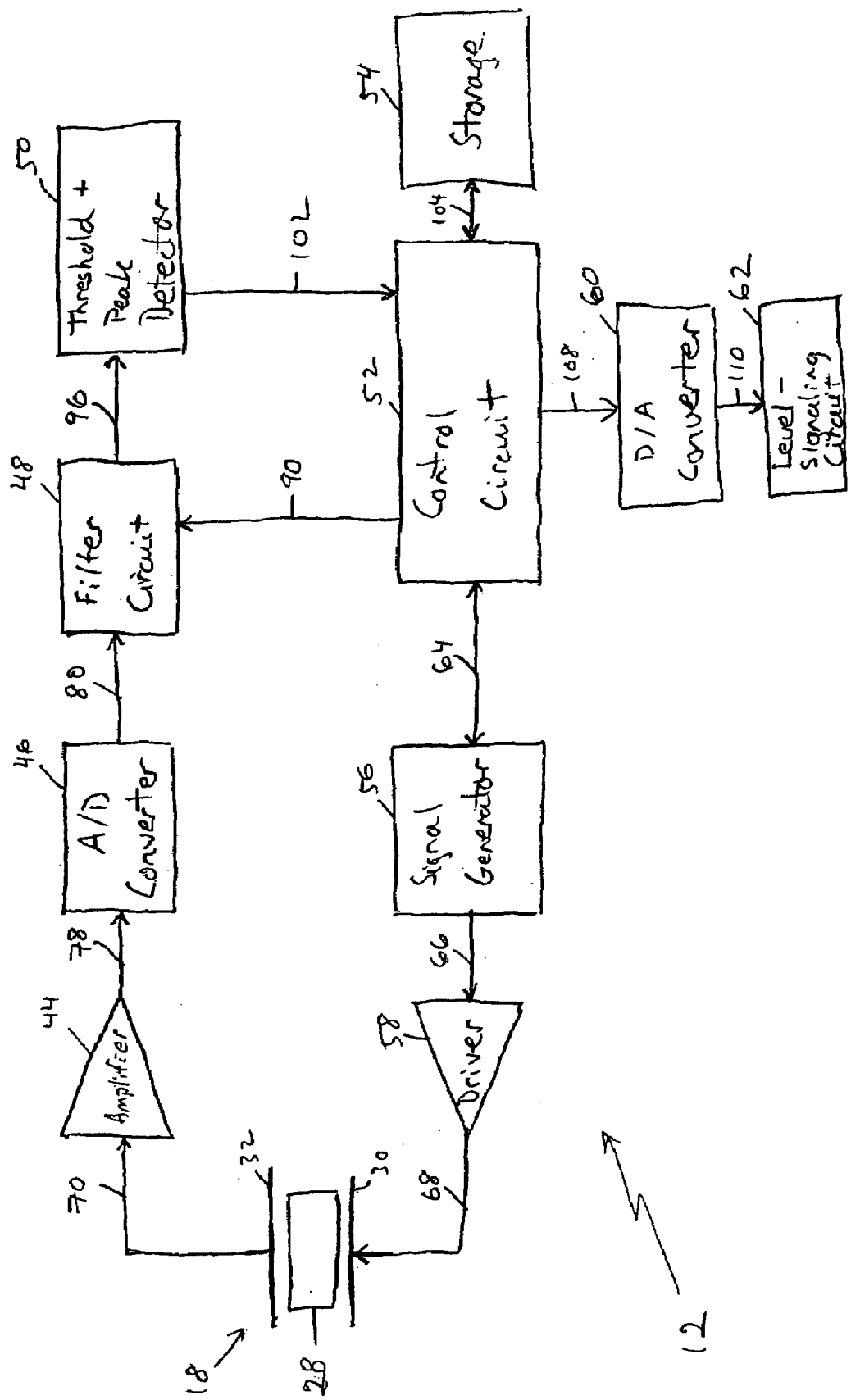
FIG. 2 is a block diagram of the ultrasonic depth determining devices depicted in FIGS. 1a and 1b.

With reference now to the illustrative drawings, and particularly to FIG. 1a, there is shown a storage tank 10 with an ultrasonic depth determining system 12 positioned at an upper portion 14 of the storage tank that contains a fluid 16. The ultrasonic depth determining system includes a transducer 18 coupled to a top surface 20 of the storage tank, which induces an ultrasonic wave 22 that propagates through a gas 24 toward the fluid in the storage tank. The depth determining system also includes a processing system 26 that drives the transducer, monitors the transducer's output, and determines the depth 27 of the fluid in the storage tank. Referring additionally to FIG. 2, the transducer is typically a piezoelectric crystal 28 having opposed silver electroplated electrodes 30 and 32, which operates as a transmitting and receiving acoustic device. The transducer is coupled to the processing system using an insulated wire 34. In contrast, FIG. 1b is an illustration of the storage tank with the ultrasonic depth determining system positioned at a lower portion 36 of the storage tank and the transducer coupled against the bottom surface 38 of the storage tank.

In the two embodiments depicted in FIGS. 1a and 1b, the transducer 18 induces an ultrasonic wave 22 in either the gas 24 or the fluid 16, which propagates toward the fluid-gas interface 40. When the wave reaches the fluid-gas interface, a portion 42 of the wave is reflected back toward the transducer located at either the upper portion 14 or the lower portion 36 of the storage tank 10. The reflected wave is sensed by the transducer and converted into electrical energy.

FIG. 2 is a block diagram of the depth determining system 12, which is used to generate the ultrasonic wave 22, detect the reflected wave 42, and determine the depth 27 of the fluid 16 in the storage tank 10. The depth determining system includes the transducer 18, an amplifier 44, an analog-to-digital ("A/D") converter 46, a filter 48, a threshold and peak detector 50, a control circuit 52, a storage device 54, a signal generator 56, a driver 58, a digital-to-analog ("D/A") converter 60, and a level-signaling circuit 62.

The control circuit 52 controls the operation of the depth determining system 12. The depth determining process begins with the control circuit providing a series of pulses on a first line 64 to the signal generator 56. In response to these pulses, the signal generator produces between approximately 4 cycles and approximately 32 cycles of a signal that can range in frequency from approximately 10 kilohertz ("kHz") to approximately 120 kHz.

The signal output from the signal generator 56 is provided on a second line 66 to the driver 58, which amplifies the signal from the signal generator and outputs a high-voltage signal having a peak-to-peak voltage that can range from approximately 100 volts to approximately 1200 volts. The high-voltage signal output from the driver is coupled via a third line 68 to one electrode 30 of the transducer 18. The high-voltage signal excites the transducer causing the transducer to vibrate, which induces a wave 22 either in the gas 24 or the fluid 16 adjacent to the transducer. The transducer is positioned and aligned so that the induced wave is directed towards an intended target, e.g., the fluid-gas interface 40 within the storage tank 10. The wave propagates through the fluid or gas in the storage tank and a portion 42 of the wave reflects off the fluid-gas interface back toward the transducer.

After the reflected wave 42 arrives at the transducer 18, the transducer converts the reflected wave's acoustic energy into electrical energy, more specifically, an electrical signal. The magnitude of the electrical energy produced by the transducer is less than the magnitude of the ultrasonic energy initially induced by the transducer due to several factors including: beam spreading, reflection losses at the fluid-gas interface 40, the acoustic impedance mismatches between the transducer and the transmission medium 16 and 24, transducer inefficiencies, and transmission loss due to the surrounding environment.

Figure 3:
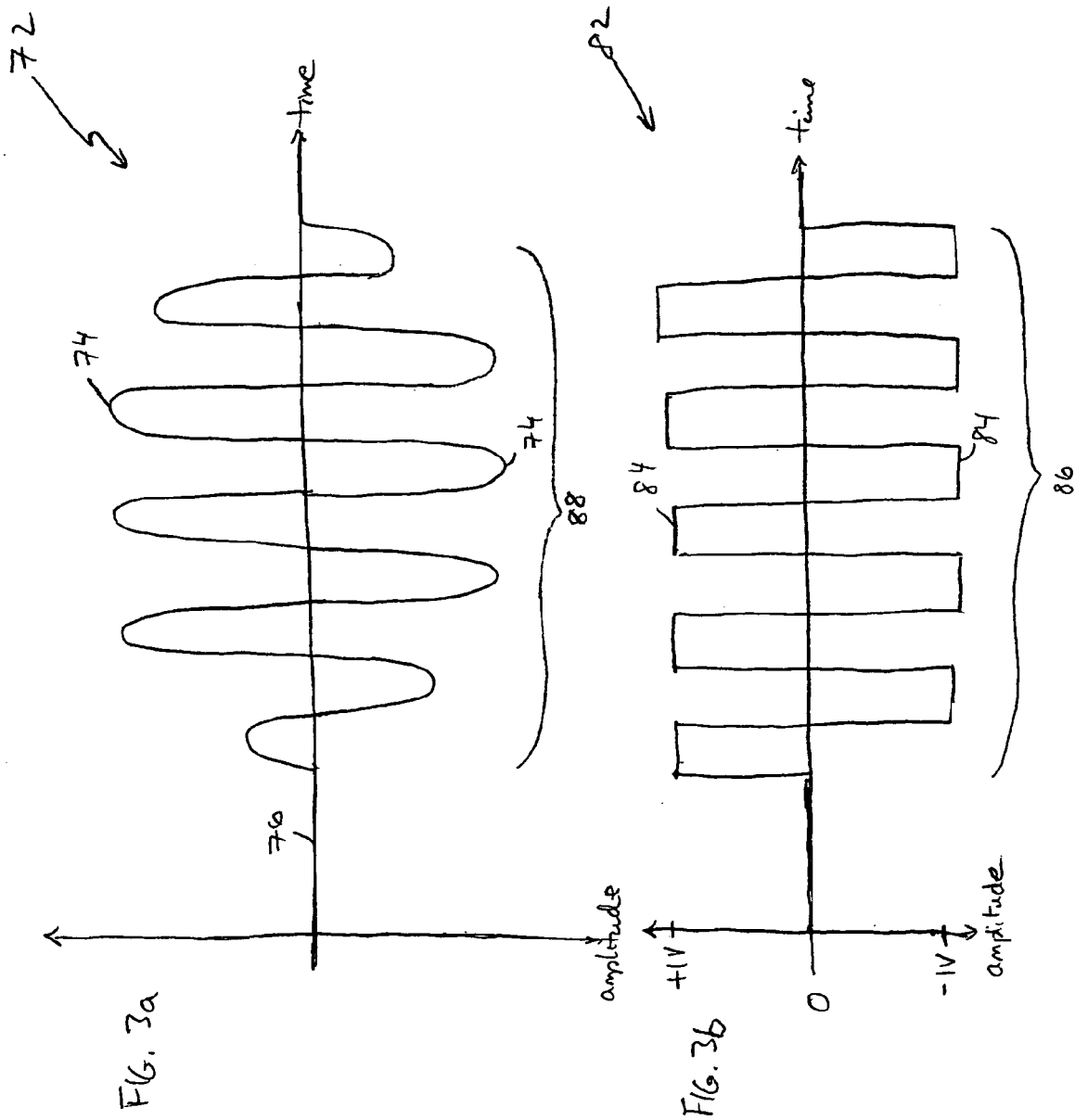
FIG. 3a is a timing diagram of a pulsed waveform generated by the transducer.
FIG. 3b is a timing diagram of a clipped reference waveform that corresponds to the pulsed waveform of FIG. 3a, and represents weighting factors for a filter.

Referring additionally to FIG. 3*a*, after the transducer 18 receives the reflected wave 42, the electrical signal produced by the transducer is provided on a fourth line 70 to the amplifier 44, which amplifies the electrical signal by a factor of at least 200 or more resulting in an amplified signal 72 having a peak amplitude 74. The amplified signal is provided on a fifth line 78 to the A/D converter 46. The amplification factor of the amplifier is selected to ensure that the signal input to the A/D converter, even when the transducer is not receiving a reflected wave, always is greater than the quantization noise, i.e., the least significant bit of the A/D converter. The amplified signal is advantageous in that it facilities a more accurate differentiation of the reflected wave's electrical signal from baseline noise 76. The amplified signal also compensates for the loss of signal strength due to the factors described above.

The A/D converter 46 samples the amplified signal 72 at a rate that is four times the frequency of the signal output from the signal generator 56 (four times the desired detection frequency) and outputs a digitized version of the amplified signal. Next, the digitized signal output from the A/D converter is provided on a sixth line 80 to the filter 48.

Referring additionally to FIG. 3*b*, a reference waveform 82 can be created by clipping the amplitude of the signal output from the signal generator 56 so that the amplitude 84 of the reference waveform only ranges in value from approximately +1 volt to approximately −1 volt. Thus, the frequency and length 86 of the reference waveform matches the frequency and length 88 of the signal output from the signal generator to the driver 58. The length of the reference waveform is provided to the filter 48 on a seventh line 90 in order to facilitate matched filtering.

Figure 4:
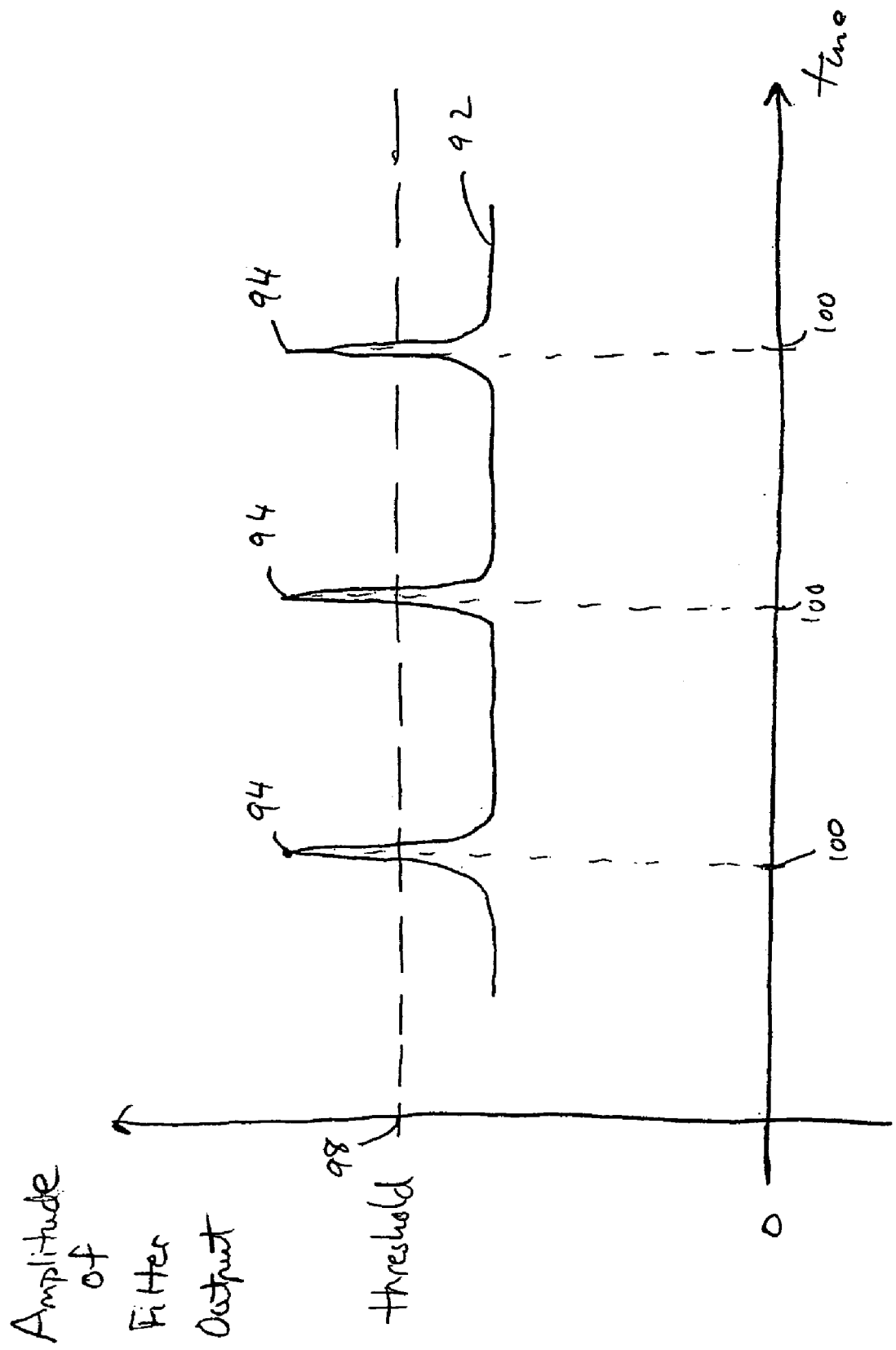
FIG. 4 is a timing diagram illustrating an amplitude of a signal output from a filter included in the ultrasonic depth determining device.

The filter 48, examples of which are discussed in detail later in this document, performs a matched filtering technique or other correlation technique in which the signal input to the filter from the A/D converter 46 is compared to the reference waveform 82. Referring additionally to FIG. 4, the filter then generates an output signal 92, which reaches a peak value 94 when the signal from the A/D converter approximates the reference waveform.

The signal 92 output from the filter 48 is provided on an eighth line 96 to the threshold and peak detector 50. Initially, the threshold and peak detector compares the amplitude of the signal output from the filter to a threshold value 98, as illustrated in FIG. 4. Next, the threshold and peak detector detects the peaks 94 of the output signal that are above the threshold value. Finally, the threshold and peak detector provides electrical signals, which include the time values 100 associated with each peak that exceeds the threshold value, on a ninth line 102 to the control circuit 52. The control circuit utilizes the time values of the peaks to calculate the depth 27 of the fluid 16 in the storage tank 10.

In another embodiment of the invention, instead of calculating the depth 27 of the fluid 16 in real time, the control circuit 52 can forward the time values 100 of the peaks 94 to the storage device 54 via a tenth line 104, for fluid depth calculations to be determined at a later time. Advantageously, only the peaks that exceed the threshold value 98 are stored in the storage device, thus, reducing the memory requirements of the depth determining system 12.

During the depth calculation, the control circuit 52 determines a roundtrip time period, which is the time between the transmission of the ultrasonic wave 22 by the transducer 18 and the receipt of the reflected wave 42 by the transducer. The control circuit can monitor the depth 27 of the fluid 16 in the storage tank 10 at predetermined time intervals based on the roundtrip time period. For example, for a particular application, the control circuit can determine that the roundtrip time period is 5 millisecond and that the fluid in the storage tank should be monitored every 30 seconds.

Embodiments of the invention include a temperature sensor (not shown), which is coupled to the control circuit 52 and located near the transducer 18. The temperature sensor is used to monitor the temperature conditions influencing the transducer. The control circuit utilizes the temperature value from the temperature sensor to calculate an adjustment to the depth measurement due to changing temperatures of the fluid 16 and/or the gas 24. For example, when the temperature is 21° C., the total distance traveled by the pulsed wave 22 from the transducer located at the top 20 of a storage tank 10 (see FIG. 1*a*) through air is d=v(sound)* t=(331.5+0.6*(21° C.)) m/sec* (0.005 sec)=1.72 meters, which includes a temperature correction. The calculated distance is divided in half since the distance between the transducer and the fluid-gas interface 40 is half the roundtrip distance traveled by the wave 22 and 42. Therefore, when the transducer is located at the top of the storage tank, the amount of fluid in the storage tank can be determined by taking the height 106 of the storage tank, e.g., 6 meters, and subtracting half the distance, d, e.g., d/2=0.86 meters, which results in a calculated value of 5.14 meters of fluid in the storage tank. Similar calculations can be performed for the embodiment illustrated in FIG. 1*b*, where the transducer is coupled to the bottom surface 38 of the storage tank.

Overall, the present invention provides an accurate measurement of the depth 27 of a fluid 16 in a storage tank 10 because the time period for propagation of the wave 22 and 42 is accurately determined using the filter 48. Only the peak values 94 output from the filter are analyzed, thus, minimizing processing needs. Also, the calculated time period is corrected for variations in temperature.

In additional embodiments of the invention, the control circuit 52 generates a pulse-width-modulated (PWM) signal that varies according to the value of the calculated depth 27 of the fluid 16 in the storage tank 10. The PWM signal is provided on an eleventh line 108 to the D/A converter 60, which transforms the PWM signal into a voltage signal ranging in amplitude between approximately 0 volt and approximately +3.3 volts. The signal output from the D/A converter is provided on a twelfth line 110 to the level-signaling circuit 62, which outputs a signal having a voltage and/or current value that correlates to the depth, or level, of the fluid in the storage tank.

In additional embodiments of the invention, the level-signaling circuit 62 is an artificial load, which transforms the voltage signal output from the D/A converter 60 into to a load current that ranges in value between approximately +4 mA and approximately +20 mA. The artificial load typically includes a bipolar junction transistor (not shown) having its base coupled to the D/A converter and its collector coupled to Vcc (+5 volts). The value of the load current produced across the artificial load is proportional to the depth of the fluid 16 in the storage tank 10. For example, a load current of approximately +20 mA corresponds to a storage tank that is full of fluid while a load current of approximately +4 mA corresponds to a storage tank that is almost empty. Accordingly, the load current can be provided to an external device (not shown), and, in doing so, provide the external device with the depth of the fluid in the storage tank.

Figure 5:
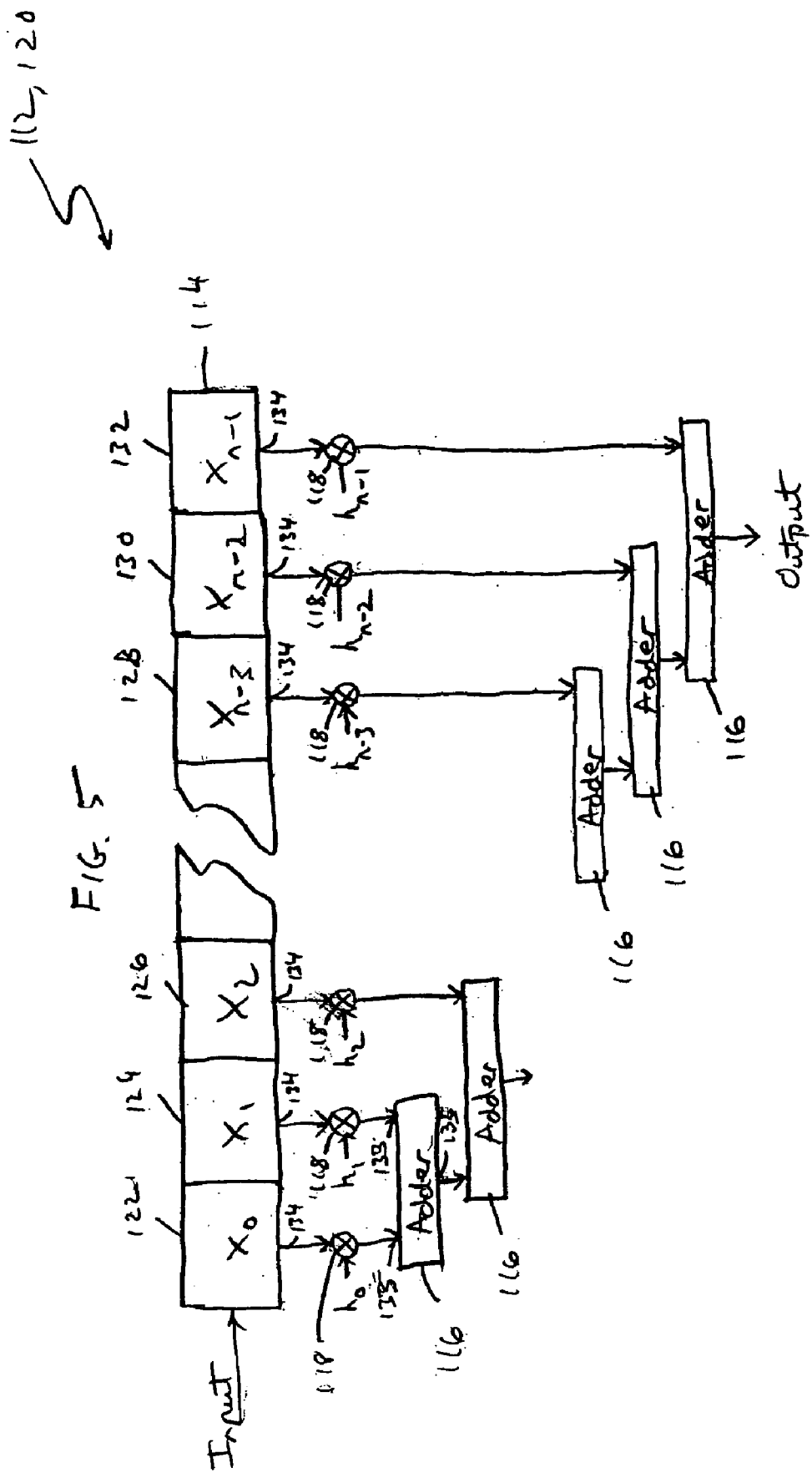
FIG. 5 is a block diagram of a filter including an n-stage shift register.

As discussed above, the filter 48 is used to determine the roundtrip propagation time of the wave 22 and 42 from the transducer 18, to the fluid-gas interface 40, and back to the transducer. Referring additionally to FIG. 5, the filter can include digital filters 112, however, there are limitations associated with the use of digital filters. In particular, most low-cost processors (not shown) lack the clock speed and the memory space required to implement classical digital signal processing ("DSP") techniques, which are used in digital filters to improve signal detection and noise immunity.

Two approaches commonly are used to implement a digital filter 112. The first approach is to use a shift register 114 in combination with adders 116 and multipliers 118 that are structured to do addition and multiplication operations, respectively. These are called DSP processors. DSP processors run at high clock speeds, and thus, consume more power than is typically available for level measurement applications. Another disadvantage associated with DSP processors is their high cost.

In the second approach, the electrical signals generated from the transducer 18 based on the reflected wave 42 are stored in memory 54, and, at a later time, are processed using a low-speed processor (not shown). This method disadvantageously requires additional storage, which adds to the overall cost of the depth determining system 12.

Embodiments of the present invention include a version of a finite impulse response ("FIR") filter 120, which is used to detect sinusoidal signals. The classical implementation of a FIR filter, illustrated in the block diagram of FIG. 5, includes an n-stage shift register 114 for the receipt of a sequence of input samples, where each stage is m samples wide, e.g., m equals 8, 10, or 12. Each stage 122–132 of the shift register has a tap 134 that is coupled to a multiplier 118, which multiplies the value of data in each stage of the shift register by a respective weighting factor, $h_i$, where i is the reference number of the stage in the shift register. The outputs of the n multipliers are summed together using n–1 adders 116, each adder having two input terminals 133 and an output terminal 135, resulting in the filter's output signal. Accordingly, for an n-stage shift register, n multiplication operations and n–1 addition operations are required to implement the filter function for the input string of samples.

Figure 6:
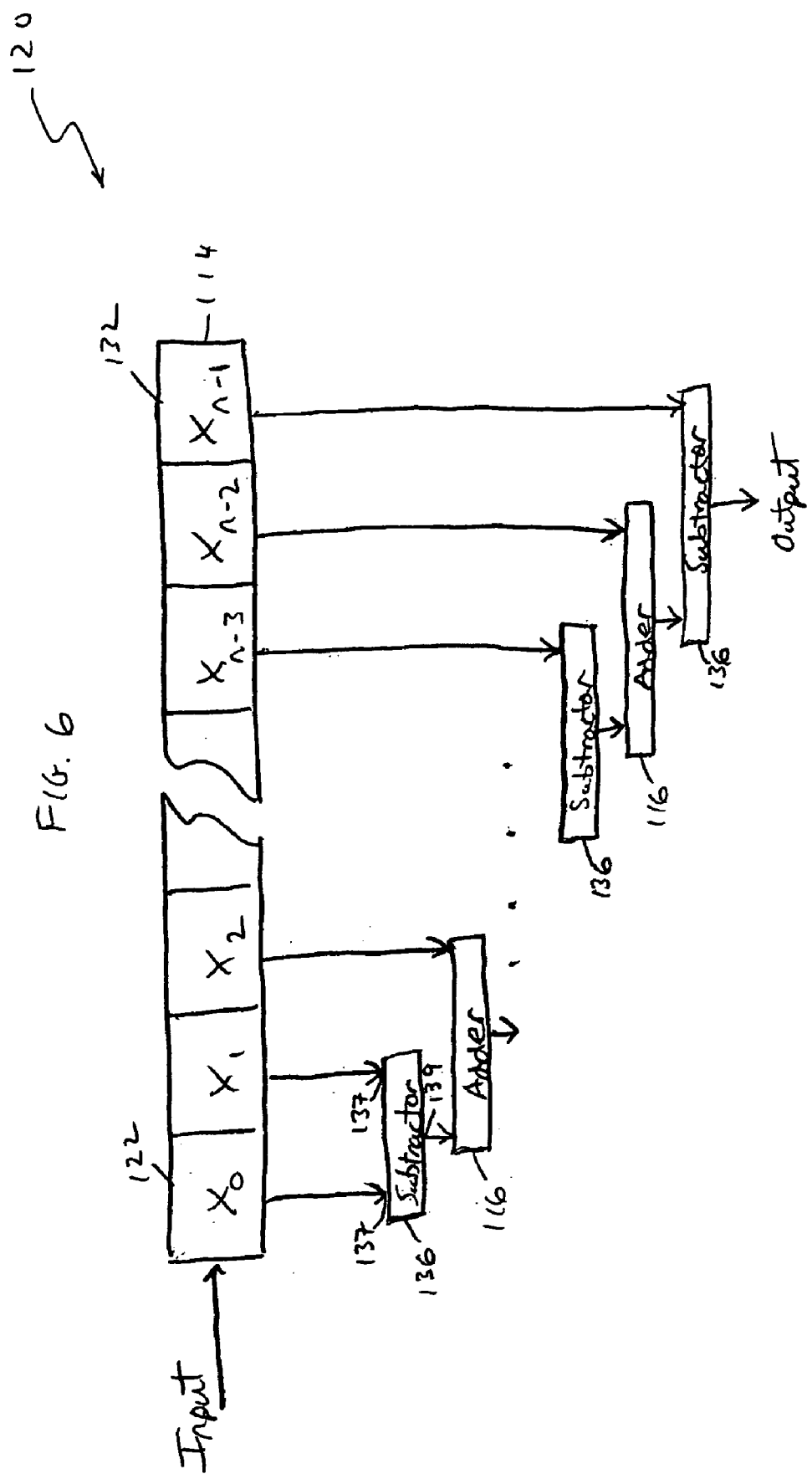
FIG. 6 is a block diagram of the filter illustrated in FIG. 5 without multipliers, where $h_0$ through $h_{n-1}$ of FIG. 5 are replaced by +1 or −1.

In the case where the signal to be detected is sinusoidal, and the data sample rate is twice the frequency of the signal desired to be detected, the weighting factors, $h_i$, can be reduced to either +1 or –1, as illustrated in FIG. 6. This results in the elimination of the multipliers 118 in FIG. 5, and every other adder 116 can be replaced with a subtractor 136, each subtractor having two input terminals 137 and an output terminal 139. Accordingly, the n multiplication operations have been eliminated, and the shift register's stage values merely are added or subtracted to produce the filter output signal. This reduces the processing steps required to produce the filter's output signal to n–1 addition and subtraction operations.

When the weighting factors, $h_i$, are +1 and –1, as illustrated in FIG. 6, the filter output can be described by the following equation:

$$\text{Output}(t_1) = \text{Input}(t_1) - (\text{Output}(t_0) + X_{n-1}(t_0))$$

where:
Output($t_0$) is the data output from the filter 120 at time $t_0$
$X_{n-1}(t_0)$ is the data in the $n^{th}$ stage 132, or last stage, of the shift register 114 at time $t_0$,
Input($t_1$) is the data input to the $0^{th}$ stage 122, or first stage, of the shift register at time $t_1$,
Output($t_1$) is the data output from the filter at time $t_1$, $t_1$ is the time at the next clock cycle after time $t_0$.

Figure 7:
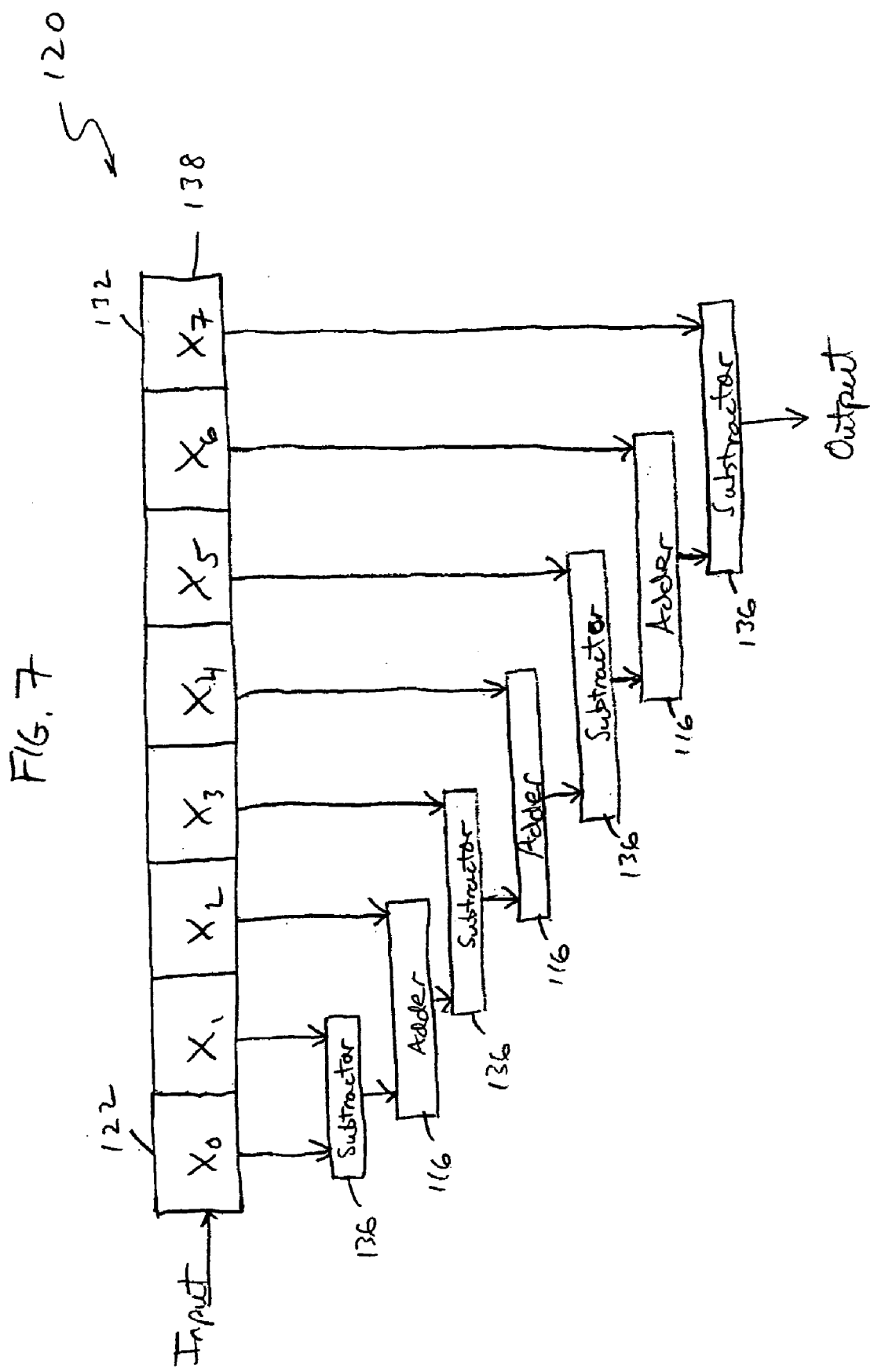
FIG. 7 is a block diagram of the filter illustrated in FIG. 6 where the n-stage shift register is an eight-stage shift register.

The above equation is derived in the following example that includes an FIR filter 120 having an eight-stage shift register 138, as illustrated in FIG. 7. The shift register has stage values $X_0(t_0)$, $X_1(t_0)$, $X_2(t_0)$, $X_3(t_0)$, $X_4(t_0)$, $X_5(t_0)$, $X_6(t_0)$, and $X_7(t_0)$ at a particular point in time, $t_0$, and the output of the filter is:

$$\text{Output}(t_0) = X_0(t_0) - X_1(t_0) + X_2(t_0) - X_3(t_0) + X_4(t_0) - X_5(t_0) + X_6(t_0) - X_7(t_0)$$

After the next clock cycle, at time $t_1$, the eight stages in the shift register 138 have values $X_0(t_1)$, $X_1(t_1)$, $X_2(t_1)$, $X_3(t_1)$, $X_4(t_1)$, $X_5(t_1)$, $X_6(t_1)$, and $X_7(t_1)$. Where $X_0(t_1)$ is the most recent data input to the shift register. The output of the filter 120 at time $t_1$ is:

$$\text{Output}(t_1) = X_0(t_1) - X_1(t_1) + X_2(t_1) - X_3(t_1) + X_4(t_1) - X_5(t_1) + X_6(t_1) - X_7(t_1)$$

Since $X_1(t_1)=X_0(t_0)$, $X_2(t_1)=X_1(t_0)$, $X_3(t_1)=X_2(t_0)$, $X_4(t_1)=X_3(t_0)$, $X_5(t_1)=X_4(t_0)$, $X_6(t_1)=X_5(t_0)$, and $X_7(t_1)=X_6(t_0)$, the output of the filter at time $t_1$ is:

$$\text{Output}(t_1) = X_0(t_1) - X_0(t_0) + X_1(t_0) - X_2(t_0) + X_3(t_0) - X_4(t_0) + X_5(t_0) - X_6(t_0)$$

$$\text{Output}(t_1) = X_0(t_1) - (X_0(t_0) - X_1(t_0) + X_2(t_0) - X_3(t_0) + X_4(t_0) - X_5(t_0) + X_6(t_0))$$

$$\text{Output}(t_1) = X_0(t_1) - (\text{Output}(t_0) + X_7(t_0))$$

In the general case, for an n-stage shift register, the above equation is:

$$\text{Output}(t_1) = X_0(t_1) - (\text{Output}(t_0) + X_{n-1}(t_0))$$

Accordingly, the output of the filter 120 at time $t_1$ can be determined from the output at time $t_0$, the samples input to the shift register 138 at time $t_0$, and the n–1$^{th}$ stage 132 of the shift register at time $t_0$ using merely one addition operation and one subtraction operation independent of the length of the filter, i.e., the number of stages in the digital filter's shift register.

Implementing a digital filter 114 with a sample rate that is twice the signal frequency is not practical. The timing of the sample clock with respect to the phase of the signal input to the filter can result in the signal being sampled at or near it's zero crossing, and thus, the filter output can be zero or very low relative to the output when a sample is taken of the signal at its peak. To resolve this issue, referring to the block diagram of FIG. 8, two digital filters 140 and 142 are used, with one filter 142 that samples the input signal 90 degrees out of phase from the other filter 140. This can be accomplished by sampling the signal input to the A/D converter 46 at four times the desired frequency, and feeding every other sample to one of the two filters. The use of two filters that are 90 degrees out of phase with one another is commonly called a complex filter 144. The two filters shown in FIG. 8 can be, for example, the FIR filters 120 depicted in FIGS. 5, 6, and 7.

Figure 8:
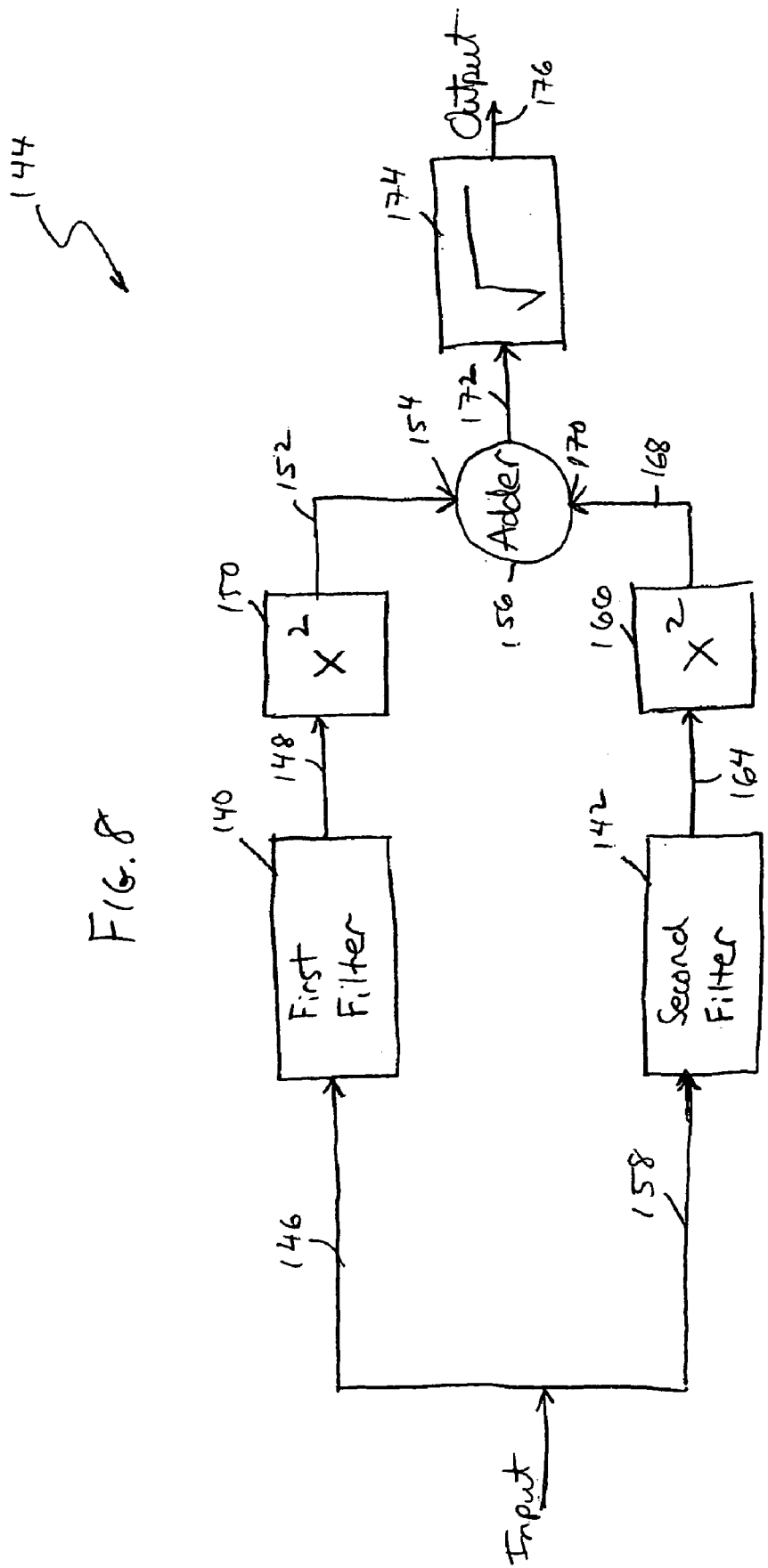
FIG. 8 is a block diagram of a complex filter.

In this embodiment, the digital filter 144 of FIG. 8 takes the place of the filter 48 illustrated in FIG. 2, and thus, the input signal in FIG. 8, is the signal output from the A/D converter 46 of FIG. 2. In this embodiment, the A/D converter is operated at four times the frequency of the signal output from the signal generator 56. The digitized input signal is provided on a thirteenth line 146 to the first filter 140. The signal output from the first filter is coupled along a fourteenth line 148 to a first circuit 150 that squares the value of the signal output from the first filter. The squared first value is supplied on a fifteenth line 152 to an input terminal 154 of an adder 156.

Also, the digitized input signal is provided from the A/D converter 46 on a sixteenth line 158 to the second filter 142. The signal output from the second filter is supplied on a seventeenth line 164 to a second circuit 166 which squares the value of the signal output from the second filter. The squared second value is supplied on an eighteenth line 168 to another input terminal 170 of the adder 156. The signal output from the adder is supplied on a nineteenth line 172 to a circuit 174 that calculates the square root of the adder's output signal. The output of the circuit that calculates the square root is provided on a twentieth line 176 that couples to the threshold and peak detector circuit 50 in FIG. 2. Accordingly, the output of the filter 144 depicted in FIG. 8 is expressed in the below equation:

$$\text{Output} = \text{SQRT}(\text{Output}_1^2 + \text{Output}_2^2)$$

where:

Output$_1$ is the signal output from the first filter 140, and
Output$_2$ is the signal output from the second filter 142.

An approximation of the square root of the sum of the squares calculation, shown in the above equation can be calculated using the following procedure. First, the absolute value is calculated for both Output$_1$ and Output$_2$. Next, the absolute value of Output$_1$ is compared to the absolute value of Output$_2$. An approximation of the output signal, Output, is determined by adding the larger of the absolute values to ⅜ times the smaller of the absolute values as indicated in the following equation:

$$\text{Output} \approx \text{Larger Output} + \tfrac{3}{8} \ast \text{Smaller Output}$$

where:

Larger Ouput is the larger of the absolute value of Output$_1$ and the absolute value of Output$_2$, and
Smaller Output is the smaller of the absolute value of Output$_1$ and the absolute value of Output$_2$.

Accordingly, when the absolute value of Output$_1$ is greater than the absolute value of Output$_2$, the value of Output is approximated by summing the absolute value of Output$_1$ and ⅜ times the absolute value of Output$_2$. Correspondingly, when the absolute value of Output$_2$ is greater than the absolute value of Output$_1$, the value of Output is approximated by summing the absolute value of Output$_2$ and ⅜ times the absolute value of Output$_1$.

Figure 9:
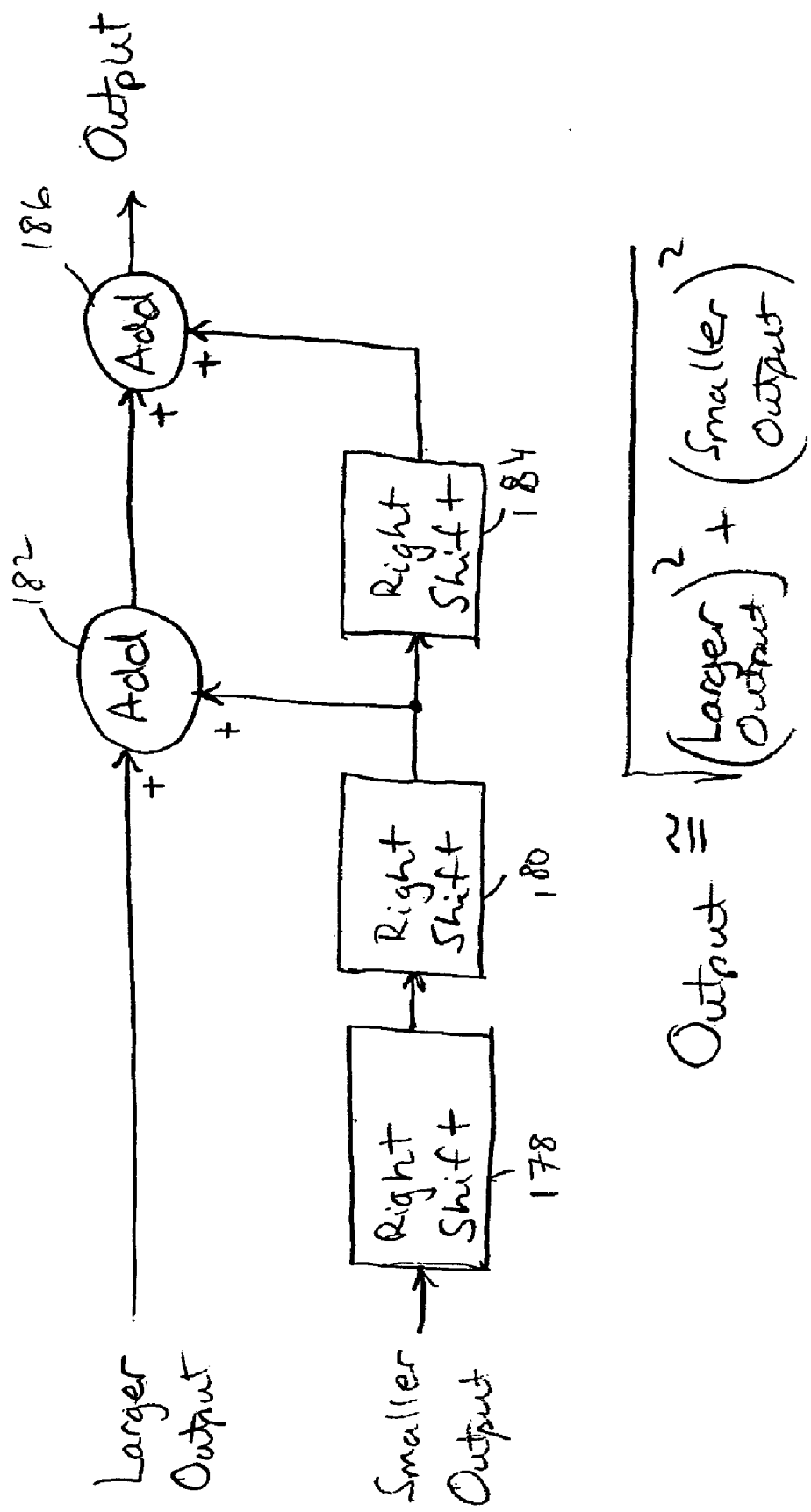
FIG. 9 is a flow diagram of an approximation that can be performed as part of the complex filter of FIG. 8.

The above approximation of the square root of the sum of the squares calculation for the Output signal can be performed instead using the procedural steps illustrated in the flow diagram of FIG. 9. More specifically, the shift register 114 and 138 of the filter, the first filter 140 for Output$_1$ or the second filter 142 for Output$_2$, is shifted twice to the right 178 and 180 for the signal, either Output$_1$ or Output$_2$, having the smaller absolute value. Next, the value of the shift register for the signal having the smaller absolute value is added 182 to the absolute value of the signal having the larger absolute value. Next, the shift register for the signal having the smaller absolute value is shifted once more to the right 184, and then added 186 to the previous sum. This procedure is used in place of the first and second circuits 150 and 166 that square the value of the filter outputs, the adder 156, and the circuit 174 that calculates the square root in the embodiment illustrated in FIG. 8.

The above embodiments of the present invention advantageously provide a simple FIR filter 120 that can be realized using only one addition operation and one subtraction operation per input sample regardless of the length of the digital filter. Also, embodiments of the present invention advantageously provide for a complex filter 144 that includes two FIR filters 140 and 142, each of which can be implemented using only one addition operation and one subtraction operation regardless of the length of the filters. Thus, the two FIR filters included in the complex filter can be implemented using only a total of two addition operations and two subtraction operations.

Figure 10:
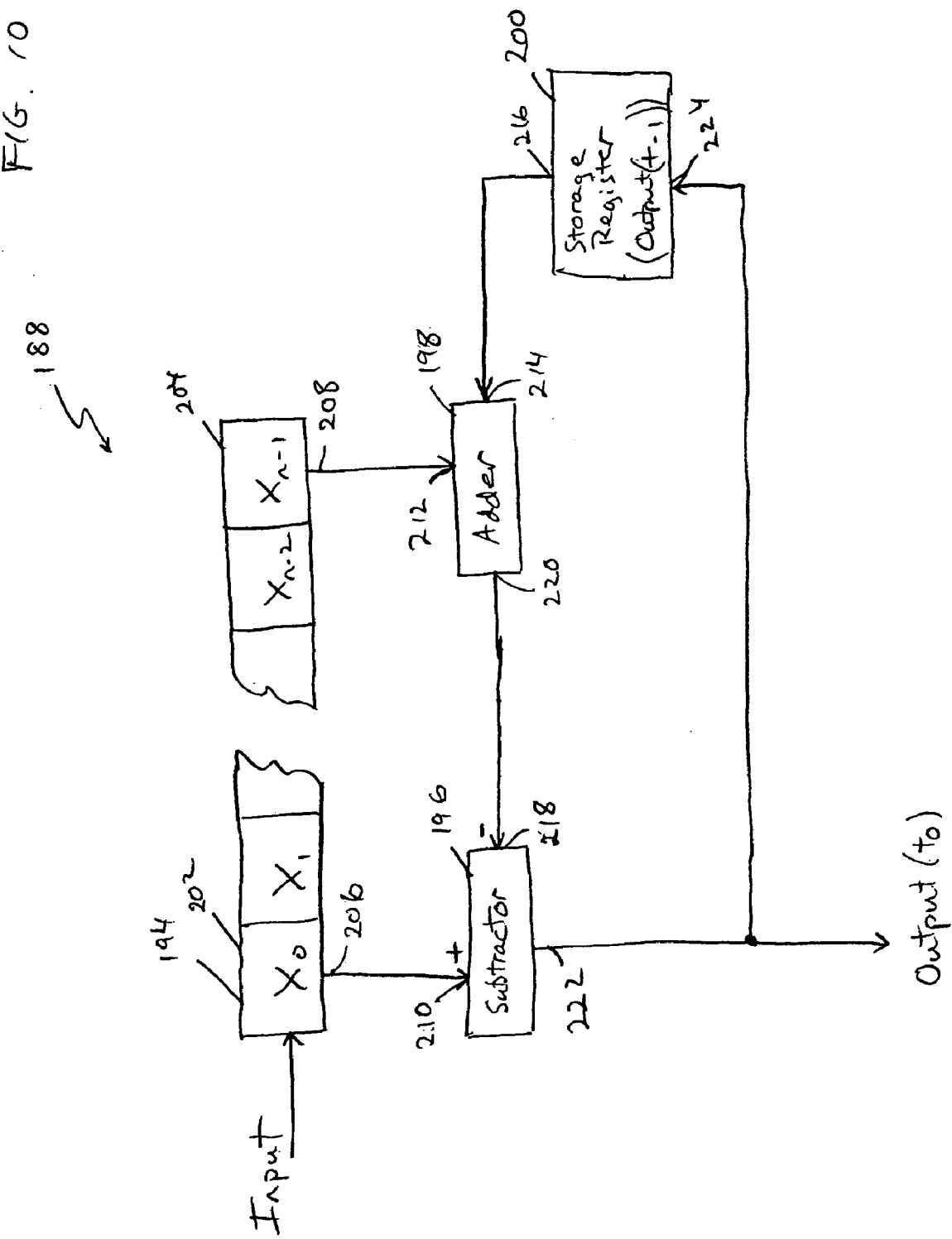
FIG. 10 is a block diagram of a filter including an n-stage shift register, a subtractor, an adder, and a storage register.

FIG. 10 illustrates another version 188 of an FIR filter 120 that is used in embodiments of the present invention to detect sinusoidal input signals. The filter illustrated in FIG. 10 is a simplification of the filter 120 depicted in FIG. 6. The filter illustrated in FIG. 10 includes an n-stage shift register 194, a subtractor 196, an adder 198, and a storage register 200. The n-stage shift register receives samples input to the filter. The first and last stages 202 and 204, respectively, of the n-stage shift register have taps 206 and 208, respectively, that are coupled to an input terminal 210 of the subtractor and an input terminal 212 of the adder, respectively. The other input terminal 214 of the adder is coupled to an output terminal 216 of the storage register, and receives the previous filter output signal (Output($t_{-1}$)) that is stored in the storage register. The other input terminal 218 of the subtractor is coupled to an output terminal 220 of the adder, and receives the output of the adder. The output signal on an output terminal 222 of the subtractor is received by the storage register at the storage register's input terminal 224. The overall output signal of the filter is the signal at the subtractor's output, which is the value in the last stage of the n-stage shift register added to the value in the storage register, and then that total subtracted from the value in the first stage of the n-stage shift register.

Figure 11:
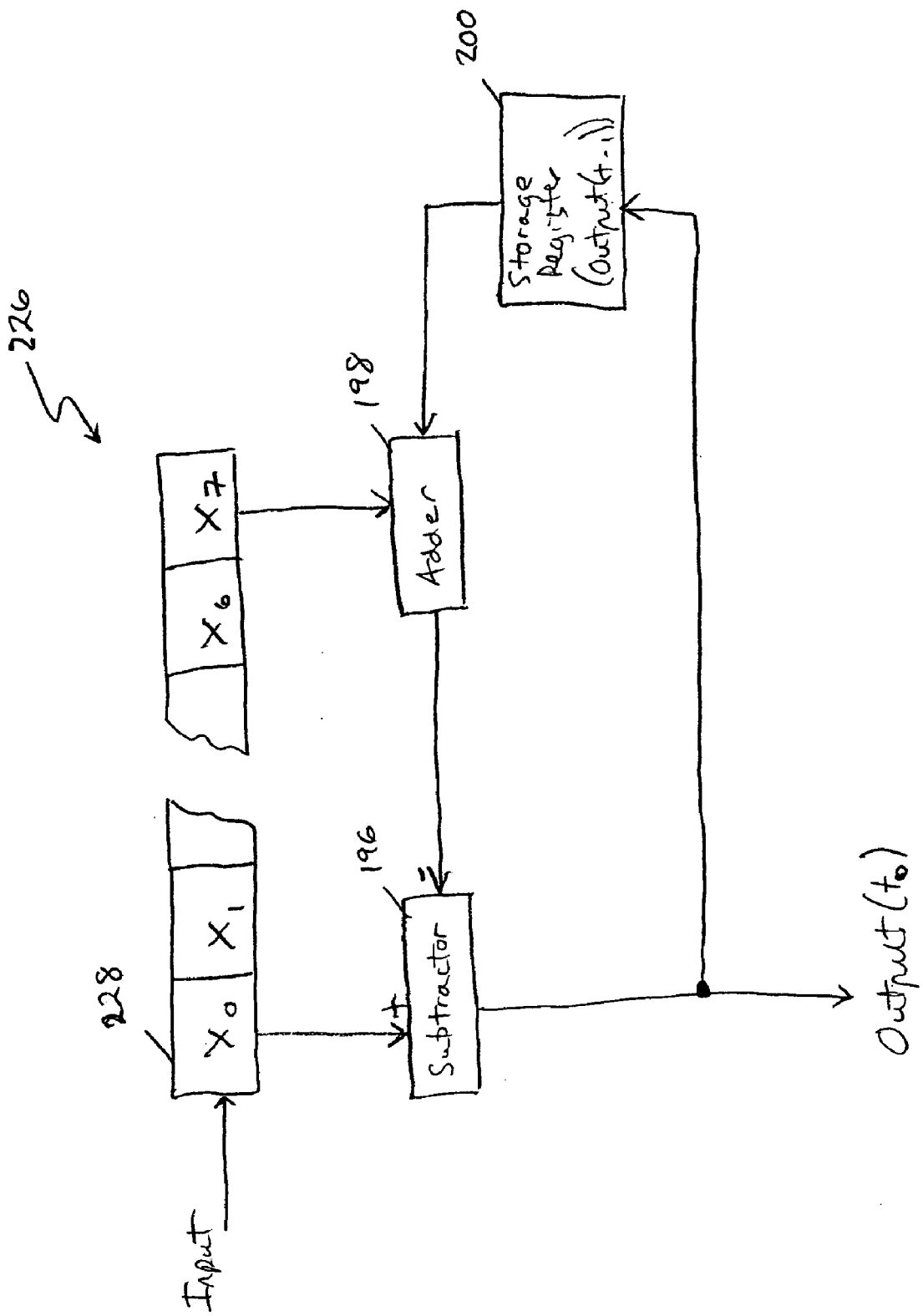
FIG. 11 is a block diagram of the filter illustrated in FIG. 10 where the n-stage shift register is an eight-stage shift register.

FIG. 11 illustrates an example case 226 of the filter 188 illustrated in FIG. 10 where n equals eight. The eight-stage shift register 228 has stage values $X_0(t_0)$, $X_1(t_0)$, $X_2(t_0)$, $X_3(t_0)$, $X_4(t_0)$ $X_5(t_0)$, $X_6(t_0)$, and $X_7(t_0)$ at a particular point in time $t_0$, and the output of the filter is:

$$\text{Output}(t_0) = X_0(t_0) - (\text{Output}(t_{-1}) + X_7(t_0))$$

Thus, the filters illustrated in FIGS. 10 and 11 advantageously reduce the total number of arithmetic operations performed by these filters in comparison to the filters 120 illustrated in FIGS. 6 and 7. Thus, the filters illustrated in FIGS. 10 and 11 are faster than the filters illustrated in FIGS. 6 and 7.

Figure 12:
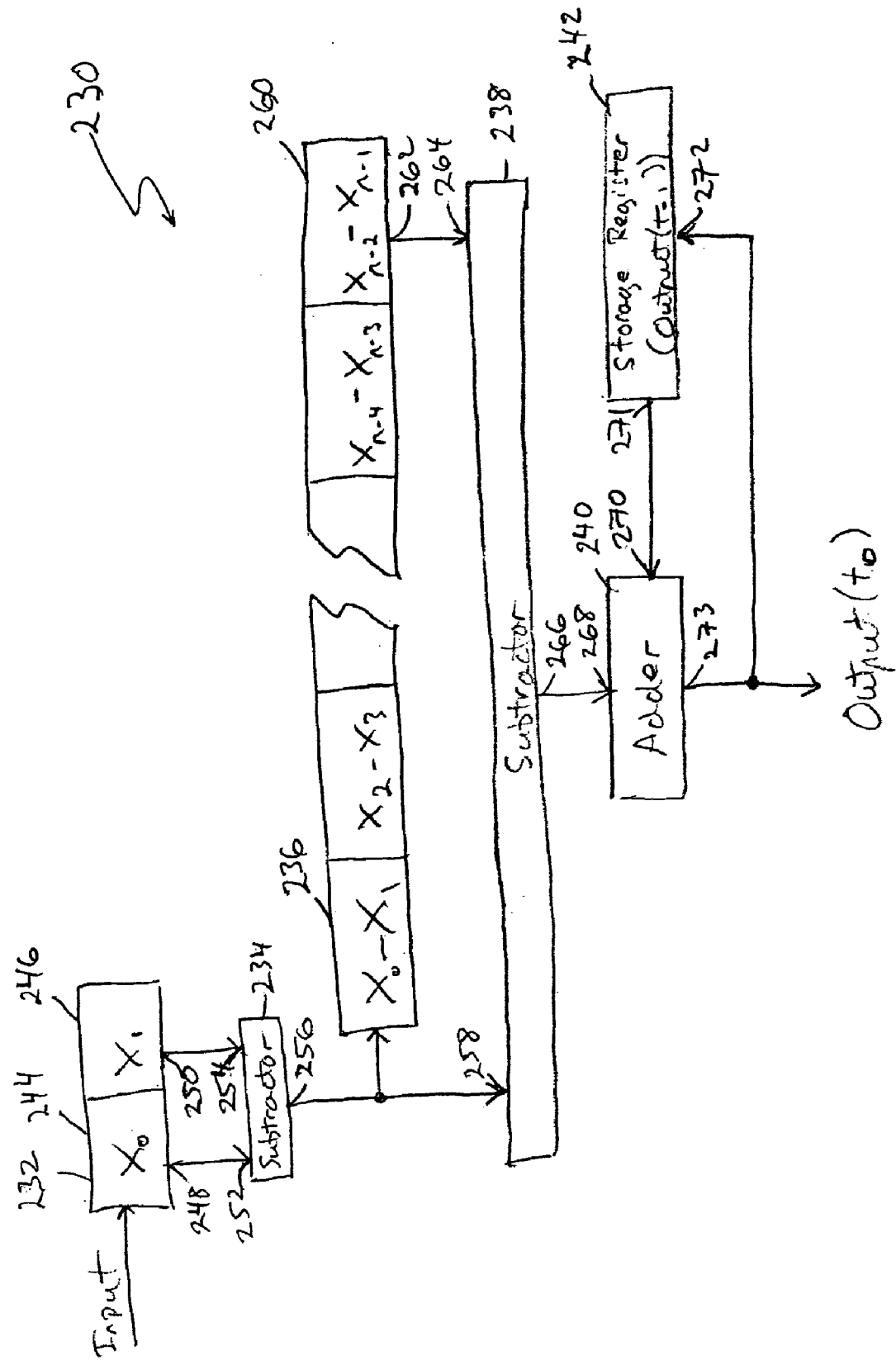
FIG. 12 is a block diagram of a filter including a two-stage shift register, a first subtractor, an n/2-stage shift register, a second subtractor, an adder, and a storage register.

FIG. 12 illustrates another FIR filter 230 that is used in embodiments of the present invention. The filter illustrated in FIG. 12 is an approximation of the filter 188 illustrated in FIG. 10. The filter illustrated in FIG. 12 includes a two-stage shift register 232, a first subtractor 234, an n/2-stage shift register 236, a second subtractor 238, an adder 240, and a storage register 242. The two-stage shift register receives samples input to the filter. Each stage 244 and 246 of the two-stage shift register has a tap 248 and 250, respectively, that is coupled to an input terminal 252 and 254, respectively, of the first subtractor, which subtracts the output of the first stage, $X_0$, from the output of the second stage, $X_1$. The output signal on an output terminal 256 of the first subtractor, i.e., $X_0-X_1$, is received by both the n/2-stage shift register and a first input terminal 258 of the second subtractor. The n/2th stage 260 of the n/2-stage shift register includes a tap 262 that is coupled to the second input terminal 264 of the second subtractor, which subtracts the output of the n/2th stage from the output of the first subtractor. An output terminal 266 of the second subtractor is coupled to a first input terminal 268 of the adder. A second input 270 of the adder is coupled to an output terminal 271 of the storage register, and an input terminal 272 of the storage register is coupled to an output terminal 273 of the adder. The overall output of the filter is the signal at the output terminal 273 of the adder, which is the value in the storage register subtracted from the value output from the second subtractor.

Figure 13:
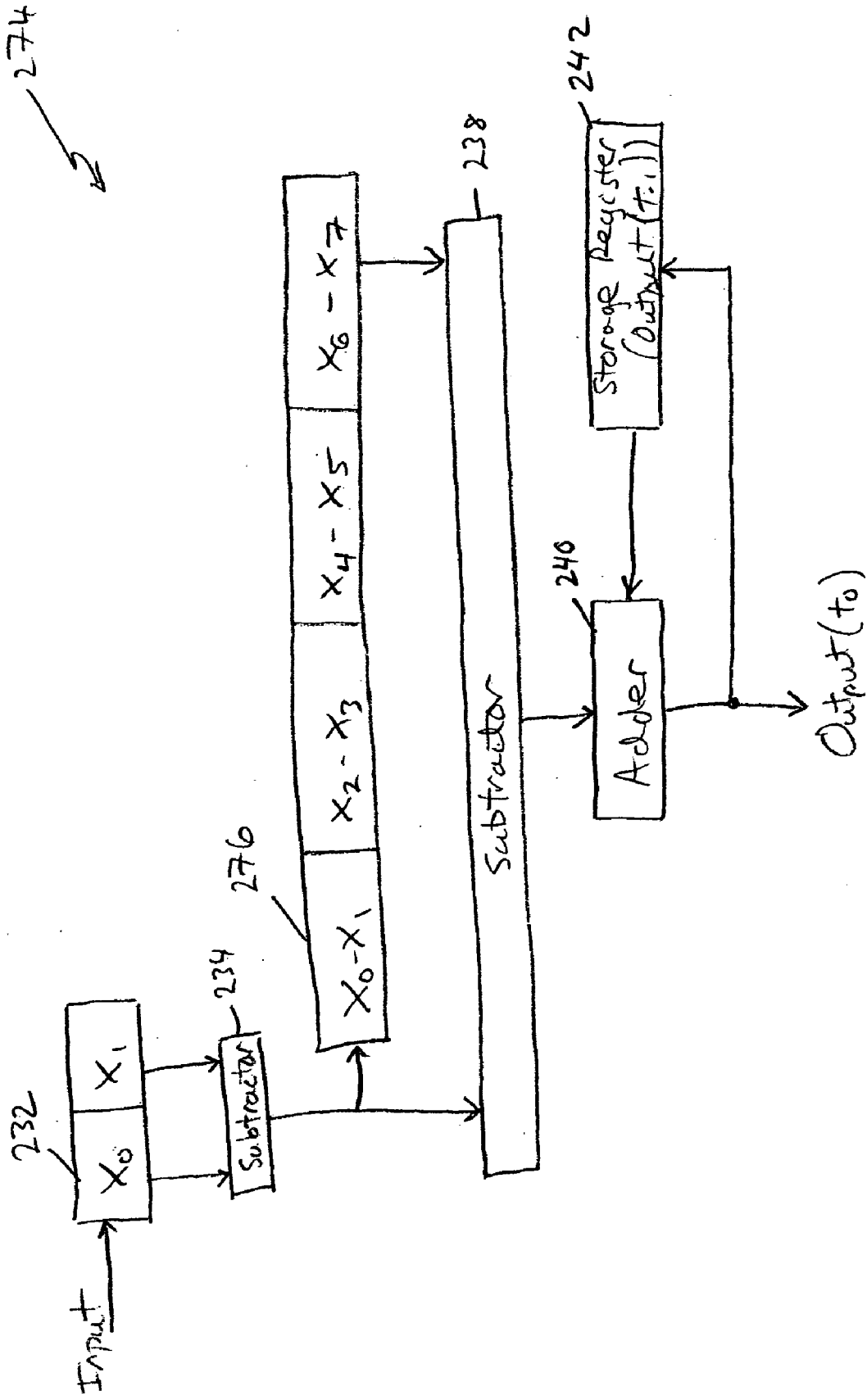
FIG. 13 is a block diagram of the filter illustrated in FIG. 12 where the n/2-stage shift register is a four-stage shift register.

FIG. 13 illustrates an example case 274 of the filter 230 illustrated in FIG. 12 where n equals eight. The four-stage shift register 276 has stage values $X_0(t_0)-X_1(t_0)$, $X_2(t_0)-X_3(t_0)$, $X_4(t_0)-X_5(t_0)$, and $X_6(t_0)-X_7(t_0)$ at a particular point in time $t_0$, and the output of the filter illustrated in FIG. 13 is:

Output($t_0$)=$X_0(t_0)-X_1(t_0)-X_6(t_0)+X_7(t_0)$+Output($t_{-1}$)

Thus, the embodiments of the filters 230 and 274 illustrated in FIGS. 12 and 13, respectively, advantageously reduce the total number of arithmetic operations performed by the filters, and thus, are faster, in comparison to the filters 188 and 238 illustrated in FIGS. 10 and 11, respectively. The advantage of filters 230 and 274 over filters 188 and 226 is that the filter is run once for every two data points received at the input ($X_0$ and $X_1$), and thus, are faster in comparison.

The filters 188, 226, 230, and 274 illustrated in FIGS. 10, 11, 12, and 13, respectively, can be the first and second filters 140 and 142 included in the complex filter 144 illustrated in FIG. 8. In which case, the sign and amplitude components of the real and imaginary terms of the input data can be examined and compared to determine a more precise alignment of the filter to the input data. Even though the complex filter is a coarse filter, an adjustment can be made after examining the sign and amplitude of the first and second filter outputs to achieve a filter output resolution equal to running the filter at full speed.

Figure 14:
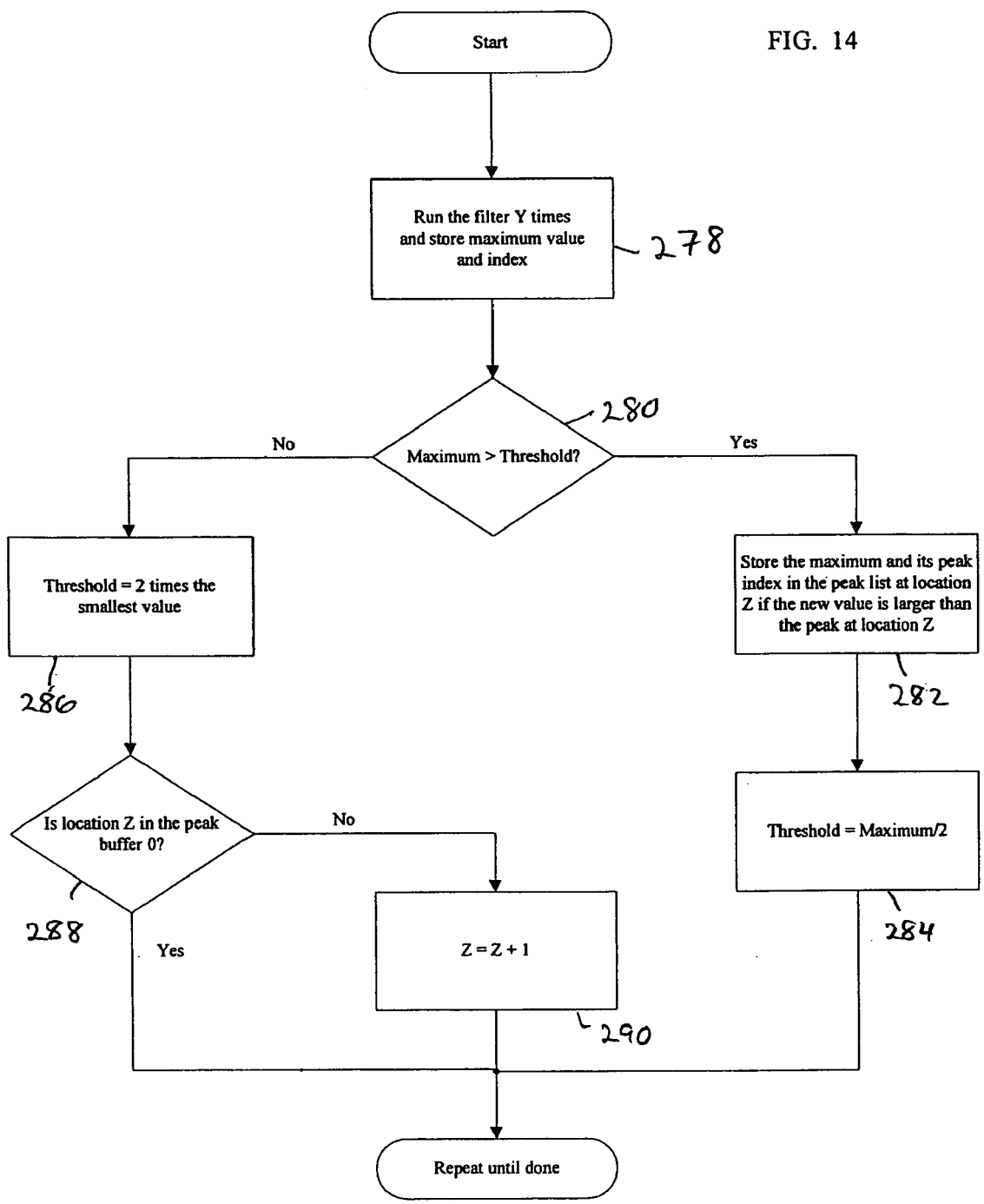
FIG. 14 is a flow diagram of a process for determining and storing peak values.

More specifically, referring to FIG. 14, signal peaks are stored in a peak buffer (not shown) included in the threshold and peak detector 50 using the following process. First, the filter is run Y times 278, and a maximum value and an index value of the maximum value of the filter output is stored during the Y times that the filter was run by the threshold and peak detector. Next, each measured maximum value is compared to a threshold value 280 by the threshold and peak detector. If the maximum value is above the threshold value 98, then the maximum value is compared to the value stored in the peak buffer 282. If the new maximum value is larger than the value in the peak list, then the maximum value and an index value, associated with the peak, that is included in a peak list is stored at memory location Z in the peak buffer. Next, the threshold value is set equal to half the maximum value 284. In this way, the threshold value is large enough to prevent the storage of erroneous maximum values, i.e., measurements of the baseline noise 76 that are incorrectly determined to be a peak. Thus, the output of the filter is stored in the peak buffer in place of the last measured peak value, and the threshold is set to half the maximum value. Next, the filter again is run Y times.

If the maximum value is not greater than the threshold value 98, then the threshold and peak detector 50 set the threshold value equal to the smaller of twice the maximum value or twice the current threshold 286. The threshold value is recalculated in this manner to avoid the detection of peaks in the baseline noise 76, and to insure detection of peaks 94 that occur later in time. Next, memory location Z of the peak buffer (not shown) is checked to see if the peak buffer location Z has a value of 0 (the peak buffer includes multiple memory address locations) 288. If so, the filter again is run Y times 278. If the memory location Z is not 0, memory location Z in the peak buffer is incremented 290 by the threshold and peak detector, so that the last peak is stored in the peak buffer and the pointer is moved to a new peak location in the peak buffer. The filter again is run Y times. Thus, when the measured maximum is not greater than the threshold, a new threshold value is calculated, and a test is performed to see if peak values were stored in the peak buffer. If so, then the peak is stored at another memory location after pointing to a new location in the peak buffer.

Figure 15:
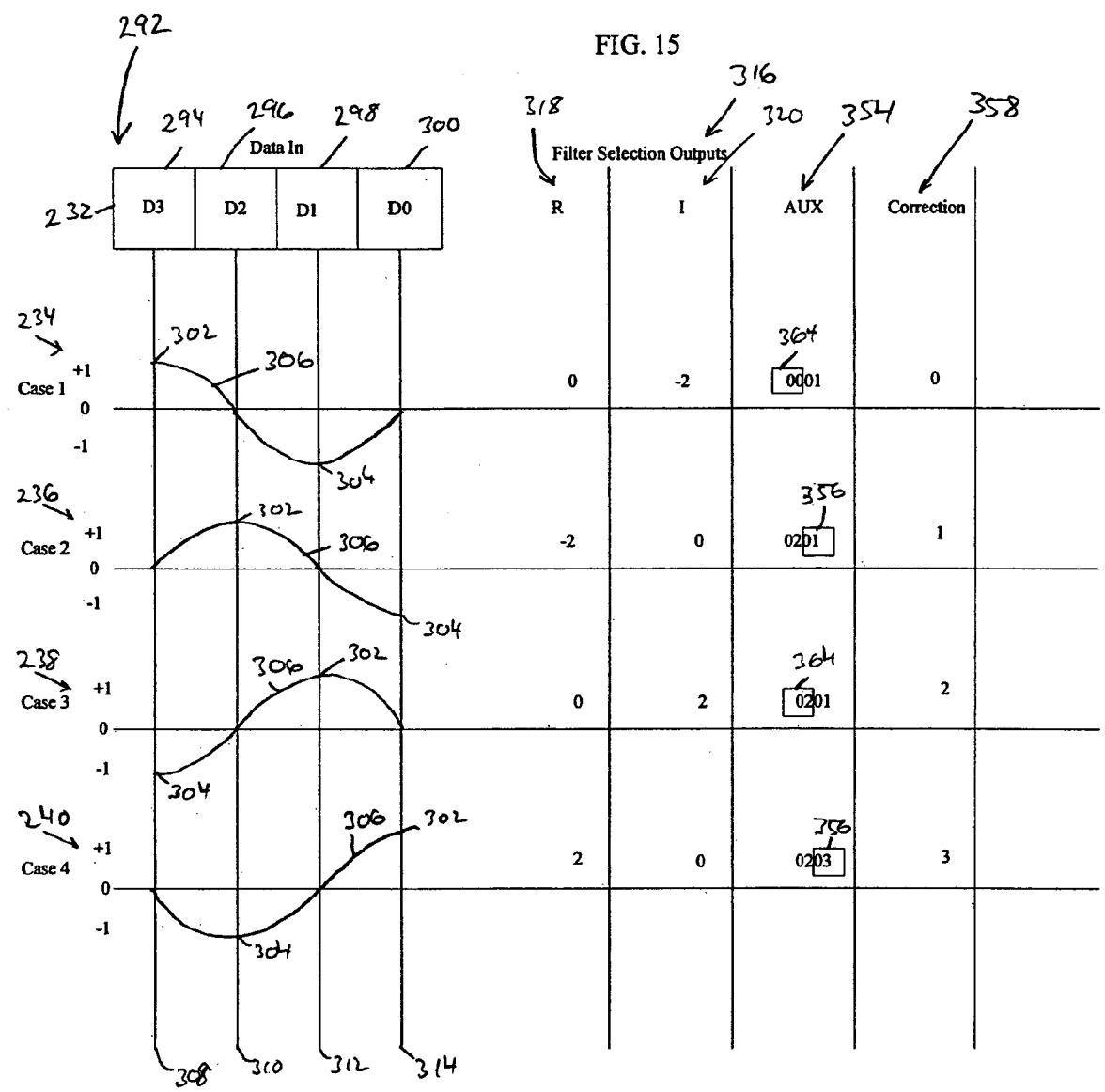
FIG. 15 is an illustration of four different cases of data input to a complex filter and the resulting real component of an input signal, imaginary component of an input signal, Aux register value, and correction for the phase difference between the input signal and the filter's assumed phase.

The previously mentioned adjustments to the filter 120, 188, 226, 230, and 274 are better understood in reference to FIGS. 15 and 16a–c. Example sinusoidal data 292 input to a four stage (n=4) filter is illustrated in FIG. 15. In particular, the four samples 294–300 of the input filter's first stage 232 are shown for four different cases 234–240. Each of the cases represents the sinusoidal input signal having a different phase delay. Each sinusoidal input signal has been sampled by the analog-to-digital converter 46 and stored in an input buffer (not shown), included in the analog-to-digital converter, at four different times as represented by data sample D0 294, D1 296, D2 298, and D3 300, where D0 is the most recent sample and D3 is the oldest sample in the input buffer. The peaks 302 and 304 of the sinusoidal input signal 306 line up with the sample times 308–314 of the input filter in the four different cases illustrated in FIG. 15.

In case 1 234, the data 292 at sample D3 294 is high and equals +1, the data at sample D2 296 equals 0, the data at sample D1 298 is low and equals −1, and the data at sample D0 300 equals 0. In case 2 236, the sinusoidal input signal 306 is delayed 90 degrees with respect to the sinusoidal input signal of case 1, and thus, the data at sample D3 is 0, the data at sample D2 is high and equals +1, the data at sample D1 equals 0, and the data at sample D0 is low and equals −1. In case 3 238, the sinusoidal input signal is delayed 90 degrees with respect to the sinusoidal input signal of case 2, and thus, the data at sample D3 is low and equals −1, the data at sample D2 equals 0, the data at sample D1 is high and equals +1, and the data at sample D0 equals 0. In case 4 240, the sinusoidal input signal is delayed 90 degrees with respect to the sinusoidal input signal of case 3, and thus, the data at sample D3 equals zero, the data at sample D2 is low and equals −1, the data at sample D1 equals 0, and the data at sample D0 is high and equals +1.

The filter selection outputs 316 shown in FIG. 15 represent the real and imaginary component 318 and 320, respectively, of the sampled sinusoidal input signal 306. Referring additionally to FIG. 8, in the general case, the real and imaginary components are the signals output from the first filter 140 and second filter 142, respectively. More specifically, in the example of FIG. 15, R, the real component of the sampled input signal, and I, the imaginary component of the sampled input signal, are determined based on the following equations:

$$R=D1-D3$$

$$I=D0-D2$$

In the complex filter scenario, the first filter filters the real component, R, of the sampled input signal and a second filter filters the imaginary component, I, of the sampled input signal.

Figure 16A:
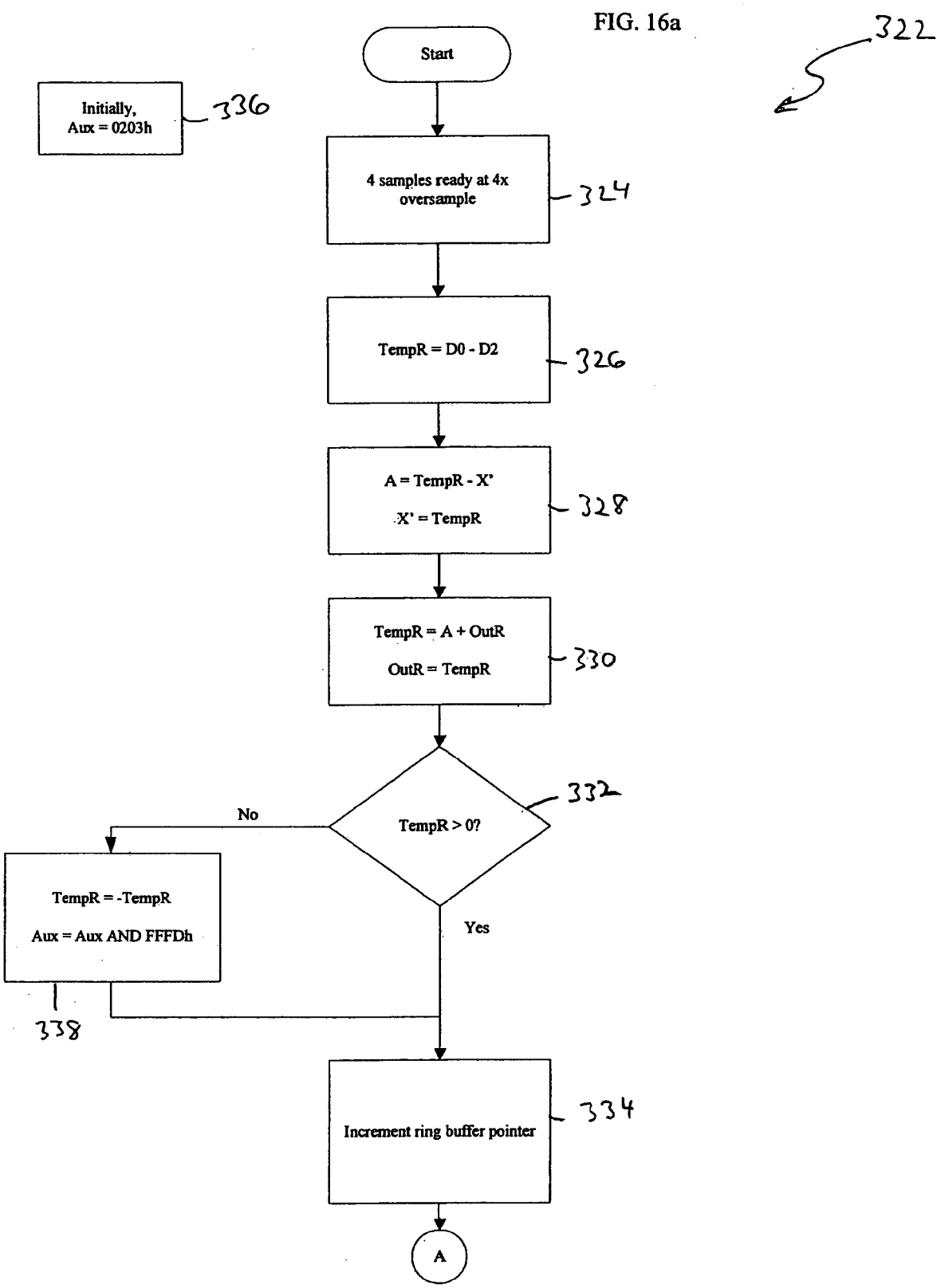
FIGS. 16a–c are flow diagrams of a process used to determine the value of the real component of the input signal, the imaginary component of the input signal, the Aux register value, and the complex filter's output.

Referring additionally to the process 322 illustrated in FIG. 16a, in one embodiment of the present invention, the number of samples taken for each time the filter is run, value Y discussed previously (see step 278 of FIG. 14), of the sinusoidal input signal 306 by the analog-to-digital converter 46 is set equal to four. The four samples of the sinusoidal input signal are taken at four times oversampling 324. Steps 326, 328, and 330 are implemented in the filter 230 of FIG. 12. In step 326, the value TempR at the output of the first subtractor 256, a temporary value for storing the real component of the sampled input signal in the memory buffer (not shown), is set equal to the value of sample D2 296 ($X_1$ at tap 250) subtracted from the value of sample D0 300 ($X_0$ at tap 248). Another value A (at the output 266 of the second subtractor 238), another temporary value, is set equal to the value X', which equals $X_{n-2}-X_{n-1}$ (at the tap 262 of the n/2th stage 260), subtracted from TempR 328. Thus, the value that is output from the two-stage buffer 190 and 244 shown in FIGS. 10, 11, 12, and 13 is subtracted from, and then placed into, TempR. Next, the value X', the last value in the shift register 236, is subtracted from the value of TempR. Then, in the next step 330, TempR is set equal to A added to the value of OutR, the output of the filter, which is stored in the storage register 242 and equals the real component of the filter's output from the last time the filter was run. Next, the OutR value is set equal to the value of TempR.

Next, the value of TempR is checked to see if it is positive 332. If the value of TempR is greater than 0, Temp R is positive, and the ring buffer pointer is incremented 334. If the value of TempR is not greater than 0, then value of TempR is negated, i.e., TempR equals the negative of TempR, the value of Aux, which is initially set equal to the hex value of 0203 336, is set equal to the value of Aux anded with the hex value FFFD 338, and then, the ring buffer pointer is incremented. Thus, if TempR is not greater than 0, the value of TempR is negative, the value of TempR is inverted and the correction register, i.e., the Aux register, is adjusted by anding the value in the Aux register with FFFD to reset bit 1 of the Aux register.

Figure 16B:
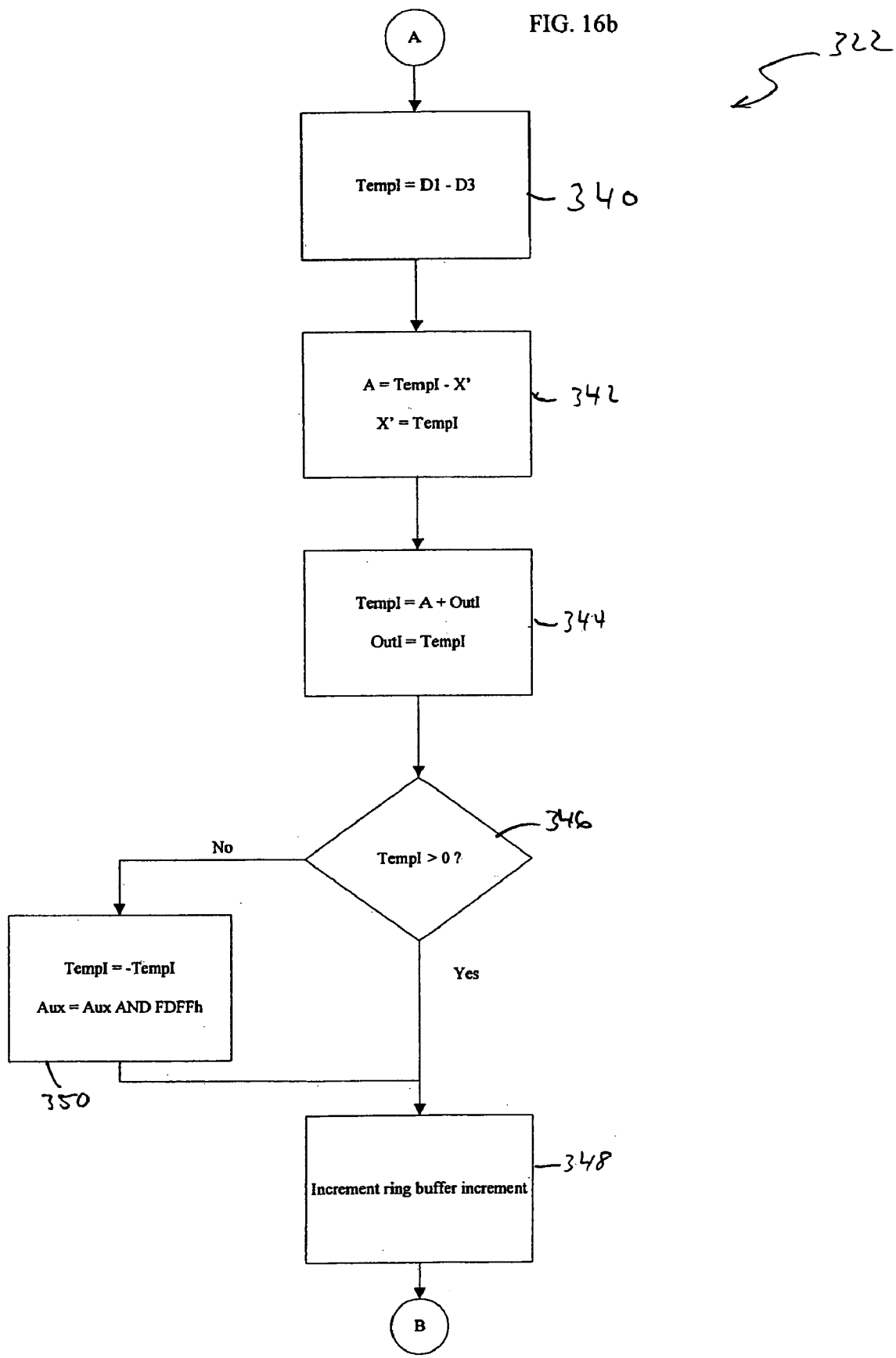

Next, referring to FIG. 16b, the imaginary component 320 is calculated by again implementing the filter of FIG. 12 using data input values D1 298 and D3 294, as was discussed previously for the real component using input values D0 300 and D2 296. The second filer 142 is use to implement the steps 340, 342, and 344 in FIG. 16b.

Next, the value of TempI is compared to the number 0 346. If the value of TempI is greater than 0, then TempI is positive, and the ring buffer pointer is incremented 348. If the value of TempI is not greater than 0, then the value of TempI is inverted, the Aux value is anded with the hex value FDFF 350, and the ring buffer pointer is incremented.

Figure 16C:
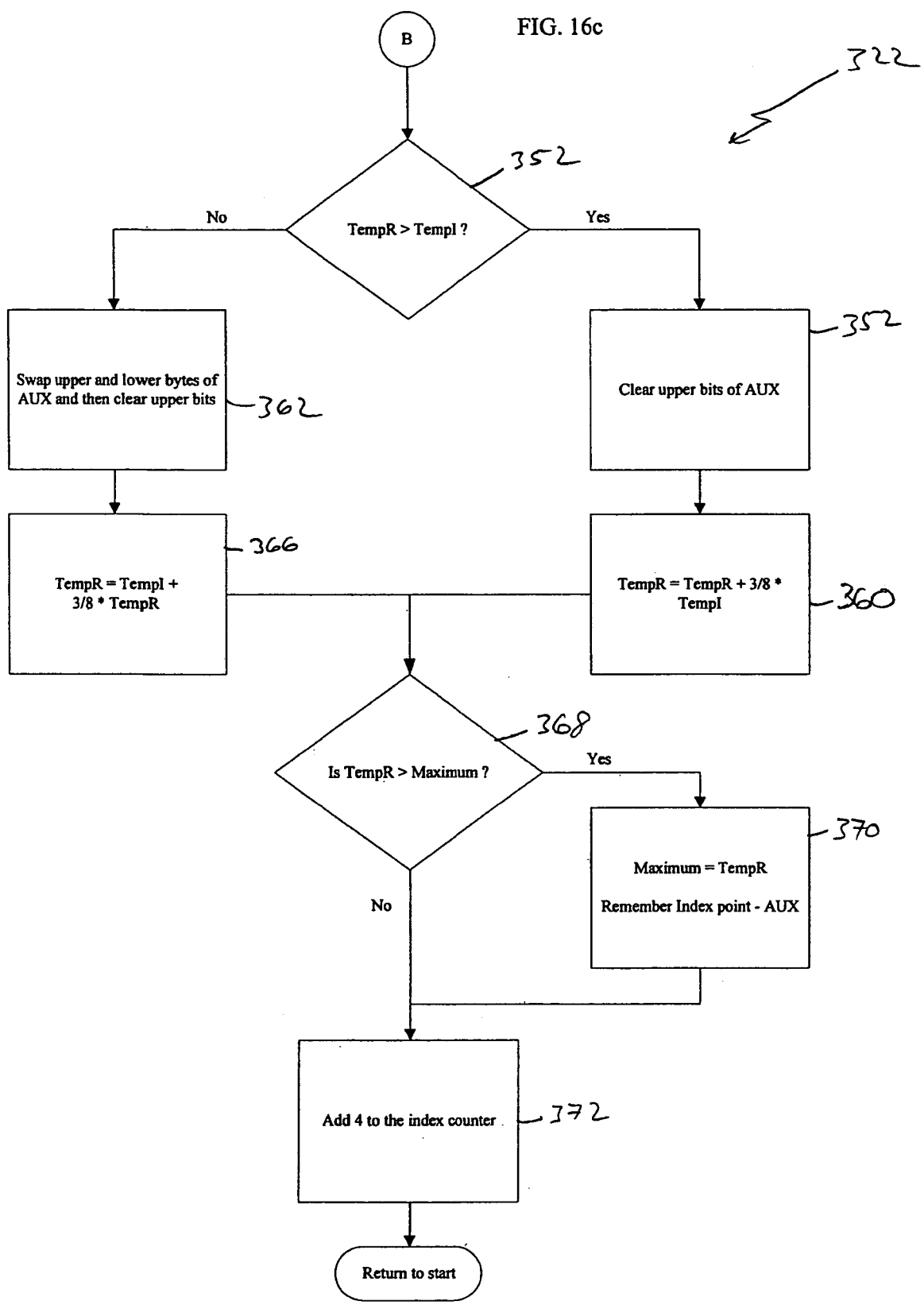

Next, referring to FIG. 16c, the value of TempR is compared to the value of TempI 352. If the value of TempR is greater than the value of TempI, then the two upper bits of the Aux register are cleared 354. This process can be seen in the example case 2 236 and example case 4 240 of FIG. 15, where the magnitude of the real component of the filter's output is greater than the imaginary component of the filter's output, and the lower two bits of the Aux register 354 within the square 356 are kept and the upper two bits of the Aux register are cleared resulting in the correction values 358. Referring additionally to FIG. 9, the value of TempR is set equal to the value of TempR added to three eights of the value of TempI 360 to approximate a square root of a sum of squares calculation.

Correspondingly, if the value of TempR is not greater than the value of TempI, the upper two bits of the Aux register are swapped with the lower two bits of the Aux register, and the resulting upper two bits of the Aux register are cleared 362. This process can be seen in the example case 1 234 and example case 3 238 of FIG. 15, where the upper two bits of the Aux register, within the square 364, are swapped with the lower two bits of the Aux register, and only the resulting lower two bits of the Aux register, i.e., the two bits within the square, are kept and the upper two bits of the Aux register are cleared resulting in the correction values 358. Next, referring additionally to FIG. 9, the value of TempR is set equal to the value of TempI added to three eights of the value of TempR 366 to approximate a square root of a sum of squares calculation. By checking the value of the real component, TempR, and the imaginary component, TempI, it can be determined whether the peak occurred at sample D0 294, D1 296, D2 298, or D4 300.

The resulting correction values 358 shown in FIG. 15 indicate the amount of difference in alignment, i.e., difference in phase, between the assumed phase of the filter when constructed, defined by the coefficients that define the filter, and the sinusoidal input signal 306. Referring additionally to FIG. 5, $h_0$ was assumed to be +1 for the further reductions in the filter complexity shown in FIGS. 6, 10, and 12. No correction is needed for case 1 234, a correction of 1 is needed for case 2 236, a correction of 2 is needed for case 3 238, and a correction of 3 is needed for case 4 240. Thus, the correction value can be used by the system 12 to more precisely align the sample times of the analog-to-digital converter and the input data.

Next, the value of TempR is compared to the peak maximum value 368. If TempR is greater than the maximum value, then the maximum value is set equal to the value of TempR and value of the AUX register is subtracted from the index pointer 370. Thus, the index counter is corrected by subtracting the value of the Aux register. Next, four is added to the index pointer 372. If the value of TempR is not greater than the maximum value, then four is added to the index counter.

Advantageously, embodiments of the present invention provide for the use of a filter structure that allows the filtering and threshold process to be performed in real time, thus, reducing the memory storage requirements without the need of a high-speed processor. Since the depth detection system 12 does not require a high-speed processor, a lower-cost low-speed processor can be used. Also, embodiments of the filter 48 according to the present invention provide for improved signal detection and high immunity to noise.

The foregoing detailed description of the present invention is provided for purposes of illustration, and it is not intended to be exhaustive or to limit the invention to the particular embodiments disclosed. The embodiments may provide different capabilities and benefits, depending on the configuration used to implement the key features of the invention. For example, the matched filtering technique discussed in the detailed description can be used to detect many types of signals, e.g., a radar signal or an infrared signal, which may be transmitted from an external source. Depending upon the characteristics of the signal, only a subset of the components included in the depth determining system 12 illustrated in FIG. 2 would be used detect and filter the signal. Furthermore, additional components, beyond those depicted in FIG. 2, may be used to implement the matched filtering technique. Accordingly, the scope of the invention is defined only by the following claims.

What is claimed is:

1. A system for determining the depth of a fluid in a storage tank, wherein the depth of the fluid is determined after the detection of a pulsed wave that is reflected from the top surface of the fluid, the system comprising:
   a. a transducer configured to measure the reflected pulsed wave and to generate an analog input signal that corresponds to the reflected pulsed wave;
   b. an analog-to-digital converter that is coupled to the transducer, and configured to convert the analog input signal into a digital input signal; and
   c. a filter that is coupled to the analog-to-digital converter, wherein the filter includes a finite impulse response filter that is configured to receive the digital input signal and to generate a digital output signal, the finite impulse response filter including:
      i. a two-stage shift register,
      ii. a first subtractor that is coupled to the two-stage shift register,
      iii. an n/2-stage shift register that is coupled to the first subtractor, where n is an even integer greater than or equal to four,
      iv. a second subtractor that is coupled to both the first subtractor and the n/2-stage shift register,
      v. an adder that is coupled to the second subtractor, and
      vi. a storage register that is coupled to the adder.

2. The system according to claim 1, further comprising:
   a. a threshold and peak detector coupled to the filter, where the threshold and peak detector is configured to compare an amplitude of the digital output signal from the finite impulse response filter to a threshold value, and to create a list of peaks, including an amplitude value and a time of each peak that exceeds the threshold value, in real time;
   b. a control circuit that is coupled to bath the filter and the threshold and peak detector, where the control circuit is configured to receive the list of peaks from the threshold and peak detector; and
   c. a storage device coupled to the control circuit that is configured to store the list of peaks received by the control circuit.

3. The system according to claim 2, further comprising:
   a. a signal generator that is coupled between the control circuit and the transducer, and that is configured to generate a generator signal that is used to stimulate the transducer to induce the pulsed wave; and
   b. a driver coupled between the signal generator and the transducer that is configured to amplify the generator signal before the generator signal is coupled into to the transducer.

4. The system according to claim 3, wherein the filter includes a matched filter that is configured to compare the analog input signal to the generator signal.

5. The system according to claim 2, wherein the control circuit calculates a value of the depth of the fluid in the storage tank based on the list of peaks, and the control circuit generates a digital pulse-width-modulated signal that varies in modulation based on the depth of the fluid in the storage tank, the system further comprising:
   a. a digital-to-analog converter that is coupled to the control circuit and configured to convert the digital pulse-width-modulated signal into an analog pulse-width-modulated signal;
   b. a level-signaling circuit that is coupled to the digital-to-analog converter, and is configured to convert the analog pulse-width-modulated signal into a level-signaling output signal correlates to the depth of the fluid in the storage tank; and
   c. a temperature sensor that is coupled to the control circuit and that is configured to provide the control circuit with a temperature value for the fluid in the storage tank, wherein the control circuit adjusts the calculated value of the depth of the fluid in the storage tank based on the temperature value for the fluid in the storage tank.

6. The system according to claim 1, further comprising an amplifier coupled between the transducer and the analog-to-digital converter and configured to amplify the analog input signal.

7. The system according to claim 1, wherein:
   a. the filter includes a complex filter having a first finite impulse response filter and a second finite impulse response filter that sample the digital input signal at twice the frequency of the pulsed wave; and
   b. the sampled digital input signal filtered by the first finite impulse response filter is 90° out of phase with respect to the sampled digital input signal filtered by the second finite impulse response filter.

8. The system according to claim 7, wherein the filter calculates a square root of a sum of squares value of a signal output from the first finite impulse response filter and a signal output from the second finite impulse response filter.

9. The system according to claim 7, wherein the filter calculates an approximate value of a square root of a sum of squares value by adding the larger of an absolute value of a signal output from the first finite impulse response filter and an absolute value of a signal output from the second finite impulse response filter to $3/8$ times the smaller of the absolute value of the signal output from the first finite impulse response filter and the absolute value of the signal output from the second finite impulse response filter.

10. The system according to claim 9, wherein the approximate value of the square root of the sum of squares value is calculated by:
   a. shifting the n/2-stage shift register to the right twice for the first or second finite impulse response filter that has the smaller absolute value of output signal;
   b. adding an output of the twice right-shifted, n/2-stage shift register to the output of the first or second finite impulse response filter that has the larger absolute value, resulting in a first added value;
   c. shifting the n/2-stage shift register having the smaller absolute value of output signal once more to the right; and
   d. adding the output of the thrice right-shifted, n/2-stage shift register to the first added value.

11. The system according to claim 7, wherein the filter is configured to determine the phase difference between the digital input signal and coefficients that define the filter.

12. The system according to claim 1, wherein:
  a. the first subtractor has two input terminals and an output terminal, and each of the first subtractor's input terminals is coupled to one of the stages of the two-stage shift register;
  b. the n/2-stage shift register has an input terminal that is coupled to the output terminal of the first subtractor;
  c. the second subtractor has a first input terminal that is coupled to the output terminal of the first subtractor, a second input terminal that is coupled to the n/2th stage of the n/2-stage shift register, and an output terminal;
  d. the adder has a first input terminal that is coupled to the second subtractor's output terminal, a second input terminal, and an output terminal; and
  e. the storage register has an input terminal that is coupled to the adder's output terminal, and an output terminal that is coupled to the adder's second input terminal.

13. The system according to claim 1, further comprising:
  a. a threshold and peak detector coupled to the filter, where the threshold and peak detector is configured to compare an amplitude of the digital output signal from the finite impulse response filter to a threshold value, and to create a list of peaks, including an amplitude value and a time of each peak that exceeds the threshold value, in real time;
  b. a control circuit that is coupled to both the filter and the threshold and peak detector, where the control circuit is configured to receive the list of peaks from the threshold and peak detector, the control circuit calculates a value of the depth of die fluid in the storage tank based on the list of peaks, and the control circuit generates a digital pulse-width-modulated signal that varies in modulation based on the depth of the fluid in the storage tank;
  c. a storage device coupled to the control circuit that is configured to store the list of peaks received by the control circuit;
  d. a digital-to-analog converter that is coupled to the control circuit and configured to convert the digital pulse-width-modulated signal into an analog pulse-width-modulated signal; and
  e. a level-signaling circuit that is coupled to the digital-to-analog converter, and that is configured to convert the analog pulse-width-modulated signal into a level-signaling output signal that correlates to the depth of the fluid in the storage tank.

14. The system according to claim 13, wherein the threshold and peak detector recalculates the threshold value based on the value of the amplitude values of the digital output signal.

15. The system according to claim 13, wherein:
  a. the filter includes a complex fitter having a first finite impulse response filter and a second finite impulse response filter that sample the digital input signal at twice the frequency of the pulsed wave; and
  b. the sampled digital input signal filtered by the first finite impulse response filter is 90° out of phase with respect to the sampled digital input signal filtered by the second finite impulse response filter.

16. The system according to claim 13, wherein the filter calculates a square root of a sum of squares value of a signal output from the first finite impulse response filter and a signal output from the second finite impulse response filter.

17. The system according to claim 13, wherein the filter calculates an approximate value of a square root of a sum of squares value by adding the larger of an absolute value of a signal output from the first finite impulse response filter and an absolute value of a signal output from the second finite impulse response filter to ⅜ times the smaller of the absolute value of the signal output from the first finite impulse response filter and the absolute value of the signal output from the second finite impulse response filter.

18. The system according to claim 13, wherein the filter is configured to determine the phase difference between the digital input signal that corresponds to the reflected pulsed wave and the sampled digital signal.

19. The system according to claim 1, wherein the finite impulse response filter is configured to calculate a digital output signal at time $t_0$, Output $(t_0)$, based on (1) the digital input signal at time $t_0$, Input $(t_0)$; (2) the digital output signal at time $t_1$, Output $(t_1)$; and (3) a data value in the final stage of the n/2-stage shift register at time $t_0$, $X_{n-2}(t_0) - X_{n-1}(t_0)$, where $t_0$ is the time at the current clock cycle and $t_1$ was the time at the previous clock cycle, and Output $(t_0)$ is calculated based on the following equation:

$$\text{Output}(t_0) = \text{Input}(t_0) - \text{Input}(t_1) - X_{n-2}(t_0) + X_{n-1}(t_0) + \text{Output}(t_1).$$

20. A system for determining the depth of a fluid in a storage tank, wherein the depth of the fluid is determined after the detection of a pulsed wave that is reflected from the top surface of the fluid, the system comprising:
  a. a transducer configured to measure the reflected pulsed wave and to generate an analog input signal that corresponds to the reflected pulsed wave;
  b. an analog-to-digital converter configured to convert the analog input signal into a digital input signal; and
  c. a finite impulse response filter configured to receive the digital input signal and to generate a digital output signal, wherein the filter includes a shift register that stores a succession of values based on the digital input signal, and wherein the filter generates each successive value of the digital output signal based on (1) the previous value of the digital output signal, (2) the current value of the digital input signal, and (3) a value stored in the shift register.

21. The system according to claim 20, further comprising:
  a. a threshold and peak detector coupled to the filter, where the threshold and peak detector is configured to compare an amplitude of the digital output signal from the impulse response filter to a threshold value, and to create a list a peaks, including an amplitude value and a time of each peak that exceeds the threshold value, in real time;
  b. a control circuit that is coupled to both the filter and the threshold and peak detector, where the control circuit is configured to receive the list of peaks from the threshold and peak detector, the control circuit calculates a value of the depth of the fluid in the storage tank based on the list of peaks, and the control circuit generates a digital pulse-width-modulated signal that varies in modulation based on the depth of the fluid in the storage tank;
  c. a storage device coupled to the control circuit that is configured to store the list of peaks received by the control circuit;
  d. a digital-to-analog converter that is coupled to the control circuit and configured to convert the digital pulse-width-modulated signal into an analog pulse-width-modulated signal; and e. a level-signaling circuit that is coupled to the digital-to-analog converter, and is configured to convert the analog pulse-width-modulated signal into a level-signaling output signal that correlates to the depth of the fluid in the storage tank.

22. The system according to claim 21, wherein the threshold and peak detector recalculates the threshold value based on the value of the amplitude values of the digital output signal.

23. The system according to claim 20, wherein:
a. the filter includes a complex filter having a first finite impulse response filter and a second finite impulse response filter that sample the digital input signal at twice the frequency of the pulsed wave; and
b. the sampled digital input signal filtered by the first finite impulse response filter is 90° out of phase with respect to the sampled digital input signal filtered by the second finite impulse response filter.

24. The system according to claim 23, wherein the filter calculates a square root of a sum of squares value of a signal output from the first finite impulse response filter and a signal output from the second finite impulse response filter.

25. The system according to claim 23, wherein the filter calculates an approximate value of a square root of a sum of squares value by adding the larger of an absolute value of a signal output from the first finite impulse response filter and an absolute value of a signal output from the second finite impulse response filter to $3/8$ times the smaller of the absolute value of the signal output from the first finite impulse response filter and the absolute value of the signal output from the second finite impulse response filter.

26. The system according to claim 23, wherein the filter is configured to determine the phase difference between the digital input signal and coefficients that define the filter.

27. A system as defined in claim 20, wherein:
a. the shift register of the finite impulse response filter has n/2 stages, where n is an even integer greater than or equal to four; and
b. the finite impulse response filter further comprises:
  i. a two-stage shift register,
  ii. a first subtractor coupled to the two-stage shift register and to the n/2-stage shift register,
  iii. a second subtractor coupled both to the first subtractor and to the n/2-stage shift register,
  iv. an adder coupled to the second subtractor, and
  v. a storage register coupled to the adder.

28. A system as defined in claim 27, wherein:
a. the two-stage shift register is configured to store the current value of the digital input signal, Input $(t_0)$, and the previous value of the digital input signal, Input $(t_1)$;
b. the first subtractor is configured to determine the difference between Input $(t_0)$ and Input $(t_1)$, to produce a difference value $X_0-X_1$;
c. the n/2-stage shift register is configured to store previous n/2 successive difference values produced by the first subtractor;
d. the second subtractor is configured to determine the difference between the current difference value $X_0-X_1$ and the difference value stored in the final stage of the n/2-stage shift register, $X_{n-2}-X_{n-1}$, to produce an output value;
e. the adder is configured to determine the sum of the current output value produced by the second subtractor and the previous value of the digital output signal, Output $(t_1)$, to produce the current value of the digital output signal, Output $(t_0)$; and
f. the storage register is configured to store the previous value of the digital output signal, Output $(t_1)$ and provide it to the adder.

29. A system as defined in claim 20, wherein the finite impulse response filter is configured to calculate a digital output signal at time $t_0$, Output $(t_0)$, based on (1) the difference between the digital input signal at time $t_0$, Input $(t_0)$, and the digital input signal at time $t_1$, Input $(t_1)$; (2) a digital output signal at time $t_1$, Output $(t_1)$; and (3) the difference between the digital input signal at time $t_{n-2}$, Input $(t_{n-2})$, and the digital input signal at time $t_{n-1}$, Input $(t_{n-1})$, which is stored in the final stage of the n/2-stage shift register at time $t_0$.

* * * * *

UNITED STATES PATENT AND TRADEMARK OFFICE
CERTIFICATE OF CORRECTION

PATENT NO. : 7,098,669 B2 Page 1 of 1
APPLICATION NO. : 10/945419
DATED : August 29, 2006
INVENTOR(S) : Larry Carter It is certified that error appears in the above-identified patent and that said Letters Patent is hereby corrected as shown below:

At column 17, line 52, "bath" should be -- both --.

At column 18, line 17, after "signal" please insert -- that --.

At column 19, line 33, "die" should be -- the --.

, line 56, "fitter" should be -- filter --.

At column 20, line 48, after "the" please insert -- finite --.

, line 49, "a" (second occurrence) should be -- of --.

At column 21, line 2, after "and" please insert -- that --.

Signed and Sealed this

Fourteenth Day of November, 2006

JON W. DUDAS
*Director of the United States Patent and Trademark Office*